(12) United States Patent
Frantz et al.

(10) Patent No.: US 12,364,783 B2
(45) Date of Patent: Jul. 22, 2025

(54) AIR PURIFICATION AND SURFACE STERILIZATION SYSTEMS INTEGRATABLE INTO BUILDING STRUCTURES AND FURNITURE SYSTEMS

(71) Applicant: ARMSTRONG WORLD INDUSTRIES, INC., Lancaster, PA (US)

(72) Inventors: William H. Frantz, Elizabethtown, PA (US); Anthony L. Wiker, Lancaster, PA (US); Alexandra G. Waltemyer, York, PA (US); Meredith G. Baxter, Lancaster, PA (US)

(73) Assignee: AWI Licensing LLC, Wilmington, DE (US)

( * ) Notice: Subject to any disclaimer, the term of this patent is extended or adjusted under 35 U.S.C. 154(b) by 789 days.

(21) Appl. No.: 17/553,731

(22) Filed: Dec. 16, 2021

(65) Prior Publication Data

US 2022/0202980 A1   Jun. 30, 2022

Related U.S. Application Data

(60) Provisional application No. 63/132,815, filed on Dec. 31, 2020.

(51) Int. Cl.
*A61L 9/20* (2006.01)
*G10K 11/162* (2006.01)

(52) U.S. Cl.
CPC .............. *A61L 9/20* (2013.01); *G10K 11/162* (2013.01); *A61L 2209/12* (2013.01);
(Continued)

(58) Field of Classification Search
CPC ...... A61L 9/20; A61L 2209/12; G10K 11/162
See application file for complete search history.

(56) References Cited

U.S. PATENT DOCUMENTS

| 6,730,265 B2 | 5/2004 | Horton |
| 9,393,338 B2 | 7/2016 | Livchak |

(Continued)

FOREIGN PATENT DOCUMENTS

| GB | 2515842 A | * 1/2015 | ............. A61L 9/122 |
| JP | H06-134027 A | 5/1994 | |

(Continued)

OTHER PUBLICATIONS

International Search Report for related application PCT/US2021/063921.

(Continued)

*Primary Examiner* — Sean E Conley
(74) *Attorney, Agent, or Firm* — Patrick Sheldrake

(57) ABSTRACT

Air purification and surface sterilization systems employing ultraviolet germicidal irradiation integratable in a discrete manner into indoor occupiable spaces in buildings. The systems may be used alone or in combination. The air purification system utilizes fan-powered disinfection units equipped with an ultraviolet light source operable to deactivate airborne pathogens. The surface sterilization system utilizes ultraviolet lamp units operable to deactivate surface accumulations of pathogen. Devices of either disinfection system may be integrated into ceiling or wall systems of the building interior space, or office furniture used in such spaces. The systems have applicability to institutional, commercial, and residential facilities as some examples.

20 Claims, 18 Drawing Sheets

(52) U.S. Cl.
CPC ....... *A61L 2209/14* (2013.01); *A61L 2209/15* (2013.01); *A61L 2209/16* (2013.01)

(56) References Cited

U.S. PATENT DOCUMENTS

| | | |
|---|---|---|
| 9,696,049 B2 | 7/2017 | Metteer |
| 10,316,141 B2 | 6/2019 | Niemiec |
| 2003/0217641 A1 | 11/2003 | Palestro |
| 2008/0196860 A1 | 8/2008 | Petlach |
| 2009/0098014 A1 | 4/2009 | Longstaff |
| 2016/0303271 A1 | 10/2016 | Livchak |
| 2018/0002926 A1 | 1/2018 | Bergman |
| 2019/0292315 A1 | 9/2019 | Niemiec |

FOREIGN PATENT DOCUMENTS

| | | |
|---|---|---|
| JP | 2007-507259 A | 3/2007 |
| JP | 2014-199176 A | 10/2014 |
| KR | 2010-0105985 A | 10/2010 |
| KR | 10-1425366 B1 | 8/2014 |
| WO | WO 02/06736 A1 | 1/2002 |

OTHER PUBLICATIONS

VidaShield Brochure, Medical Illumination, 2019.
VS01 VidaShield Data Sheet, Medical Illumination, Jul. 17, 2019.

\* cited by examiner

AIR PURIFICATION AND SURFACE STERILIZATION SYSTEMS INTEGRATABLE INTO BUILDING STRUCTURES AND FURNITURE SYSTEMS

FIELD

The present invention relates to air purification and surface sterilization systems, and more particularly to such systems employing ultraviolet (UV) germicidal irradiation (UVGI) configured for integration in a discrete manner into indoor building structures such as ceiling, wall, and office furniture systems usable in occupiable spaces.

BACKGROUND

UVGI air purification and work surface sterilization lighting devices and fixtures exist to combat pathogens/microbes such as bacteria and viruses which may be airborne and/or accumulate on various surfaces within the occupiable space of a building. This creates exposure of human occupants in the building to infection and concomitantly various diseases attributable to these pathogens. Such disinfection devices, however, are typically poorly integrated into interior building structure elements such as ceilings, walls, or other building elements in an aesthetically pleasing manner. The often have an industrial look being comprised of metal housings and with shapes making them too unsightly for application in building interior spaces seeking to achieve a more refined appearance.

Improvements in air purification and surface sterilization systems which are configured for discrete and/or partially or fully concealed use in institutional, commercial, and residential buildings are desired.

SUMMARY

In one aspect, an air purification system including a fan-powered disinfection unit employing ultraviolet germicidal irradiation (UVGI) is disclosed which can be integrated in a discrete or partially/fully concealed manner within ceiling and wall systems of, for example without limitation, institutional, commercial, or residential occupiable spaces. The UV disinfection units therefore do not negatively affect the aesthetic appearance of the interior occupiable spaces within the building. In certain configurations, the disinfection units may also be integrated in a partially or fully concealed manner into furniture systems usable within the occupiable spaces. Self-supported free standing or partially anchored partition panels as commonly used in office furniture systems to construct workspace cubicles is one non-limiting example. Such partition panels are readily removable and changeable in location to configure office spaces, which therefore are readily distinguishable from permanent walls which form part of the of the building exterior or interior structural wall framing. In other embodiments, the UV disinfection units may be integrated into one or more canopy units supported freely by the ceiling in a suspended manner in numerous locations throughout the occupiable space. Other concealed applications of the UV disinfection units and air purification system are possible.

In some embodiments, the fan-powered UV disinfection units include an outer housing defining an air inlet and an air outlet. Arranged in the flow pathway between the air inlet and outlet is at least one electric fan operable for drawing air from the occupiable space of the building into the unit, and returning the air back to the space after being irradiated by an UV light source such as one or more UV lamps. In some embodiments, the lamps may be shielded to protect occupants from direct exposure to the UV light source at least while the occupiable space is occupied. The UV lamps have a wavelength selected to deactivate airborne pathogens (e.g. bacteria and viruses) in the extracted air stream before return to the space which helps minimize the risk of airborne disease transmission and cross-contamination between building occupants sharing the same space. In one embodiment, UV-C lamps (germicidal lamps) may be used which are known to be effective for inactivating airborne pathogens and those accumulating on non-porous surfaces. One or more air filters may be included upstream of the UV light source to initially pre-filter the air drawn from the occupiable space to remove large dust particles and protect the UV lamps. In some embodiments, high-efficiency air filters such as MERV (Minimum Efficiency Reporting Values) filters, electrostatic charged/enhanced particle filters, HEPA (high efficiency particulate air), true HEPA and HEPA-like filters, ULPA (ultra-low particulate air) filters or others may be used to reduce airborne pathogens. Some configurations of the system may include various configurations of an air inlet duct and outlet duct fluidly coupled between the occupiable space and the inlet and outlet respectively of the UV disinfection unit. The air inlet and outlet ducts may be configured to provide the airstream path needed for partially or fully concealed integration of the disinfection unit into the applicable ceiling or wall system or furniture system.

In other aspects, a UV surface sterilization system is disclosed which is usable with the air purification system or alone. The system generally includes a plurality of UV-C lamp units configured for discrete integration into components of the building ceiling system which may include suspended ceiling, ceiling blade system, ceiling canopies, soffits, or other structures and elements. The units are located to irradiate vertical, angled, or horizontal surfaces (e.g. flooring, task/work surfaces such as desks, counters, tables, furniture, etc.) within the occupiable space where airborne pathogens may drop our of suspension in air and accumulate, or may be deposited by direct hand contact.

The occupiable space may utilize various combinations and types of devices of both the air purification and surface sterilization systems disclosed herein to combat pathogen populations within the space and the transmission of disease. Accordingly, it will be appreciated that any of the UV-based devices disclosed may be used in any combination in various embodiments even if not explicitly shown or discussed herein. The devices disclosed herein may further be modified and customized as needed to accommodate different aspects of building construction and the occupiable space encountered without departing from the spirit of the embodiments described and shown.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the exemplary embodiments of the present invention will be described with reference to the following drawings, where like elements are labeled similarly, and in which.

Figure 1:
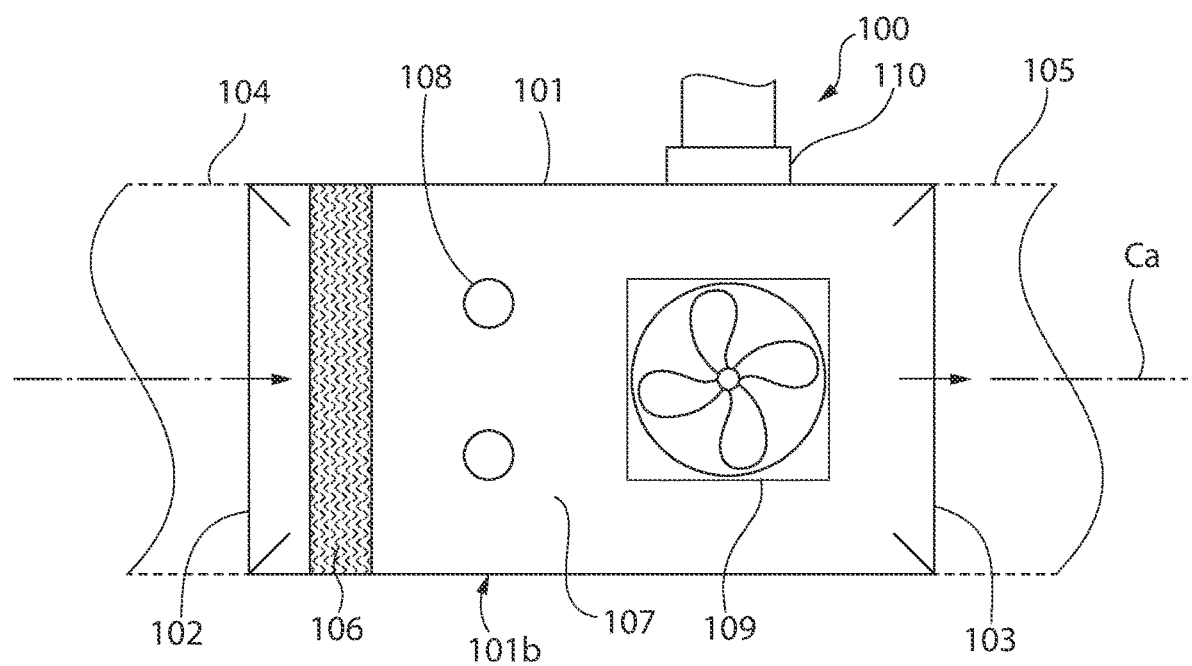
FIG. 1 is a schematic diagram of one non-limiting embodiment of a UV-based air purification disinfection unit according to the present disclosure.

All drawings are schematic and not necessarily to scale. Parts given a reference numerical designation in one figure may be considered to be the same parts where they appear in other figures without a numerical designation for brevity unless specifically labeled with a different part number and described herein.

DETAILED DESCRIPTION

The features and benefits of the invention are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range.

FIG. 1 is a schematic diagram of a non-limiting embodiment of a fan-powered UV disinfection unit 100 usable in the present air purification system disclosed herein. Disinfection unit 100 may employ ultraviolet germicidal irradiation (UVGI) to control and reduce airborne pathogen populations in an occupiable space of the building. The UV disinfection unit can be effectively integrated in a concealed manner into building features and surfaces such as without limitation ceilings, acoustical elements employed in ceiling systems and walls, and free standing or partially anchored movable wall panels or dividers in office furniture systems. These objects or elements may be used to hide the disinfection units from view within the occupiable space to be treated by the unit for improved aesthetics. Materials and parts of the system can be substituted, and geometry and form can be changed to suit the application and elements into which the disinfection units are to be integrated in a concealed manner Exemplary applications of the disinfection unit 100 to the foregoing building objects or systems are disclosed herein as non-limiting examples.

Fan-powered UV disinfection unit 100 is configured to effectively treat and inactivate airborne pathogens in the present concealed UV disinfection system applications disclosed herein. The disinfection unit 100 generally comprises a housing 101 defining centerline axis Ca, an air inlet 102 at one end of the housing, an air outlet 103 at an opposite end of the housing, and an internal cavity 107 extending axially between the ends. The inlet and outlet defines openings configured for extracting untreated air from and discharging treated air back the building occupiable space (e.g. room). Inlet 102 and outlet 103 may be arranged in any required orientation such as for example without limitation horizontally open in the direction of the centerline axis Ca as shown, vertically open perpendicular to axis Ca, at an oblique angle to axis Ca, or any combination thereof as needed depending on the spatial relation of the disinfection unit to the occupiable space.

An air inlet duct 104 and/or air outlet duct 105 may be provided and configured as needed to fluidly coupled the inlet 102 and outlet 103 of the disinfection unit 100 to the occupiable space. The ductwork facilitates concealing and integrating the disinfection unit into the building ceiling, wall, or furniture systems. Preferably, the disinfection unit is located proximate to the occupiable space in the building to minimize the length of the ductwork and concomitantly the fan power requirements and electrical energy usage. In some embodiments, the inlet and/or outlet duct 104, 105 may be omitted depending on the installed location of the disinfection unit 100 relative to the occupiable space.

At least one fan 109 is arranged in the internal cavity 107 of disinfection unit housing 101 within the airflow pathway between the air inlet and outlet. Fan 109 operates for drawing untreated air from the occupiable space into the unit 100, and returning treated (disinfected) air back to the space after being irradiated by an UV light source. The light source may comprise one or more UV-C lamps 108 in one embodiment positioned upstream of the fan 109 as shown, or in other embodiments downstream of the fan depending on whether the fan is located at the air inlet or outlet end of the housing 101. Lamps 108 may be elongated tubular bulbs in shape in some conventional offerings; however, other shaped lamp bulbs may be used. The UV-C spectrum covers electromagnetic wavelengths of 200 nm to 280 nm and is considered more effective for inactivating pathogens than UV-A or UV-B. Any suitable commercially-available UV-C lamps may be used in any suitable orientation within the disinfection unit housing 101. In some embodiments, the UV-C lamps may emit light having a wavelength of about 265 nm, which is an optimum wavelength for effective pathogen inactivation. Other wavelengths of UV-C however may be used.

The disinfection unit housing 101 is configured to fully enclose at least the UV-C lamps 109 to shield occupants within the space from direct exposure to UV light.

One or more air pre-filters 106 may be used preferably upstream of the UV-C lamps 108 to remove large dust particles present the untreated air extracted from the occupiable space. This protects the UV lamps. Conversely, air pre-filters 106 may alternatively include high-efficiency air filters such as MERV (Minimum Efficiency Reporting Values) filters, electrostatic charged/enhanced particle filters, HEPA (high efficiency particulate air), true HEPA and HEPA-like filters, ULPA (ultra-low particulate air) filters or similar may be used to reduce smaller airborne pathogens.

Housing 101 of the UV disinfection unit 100 may be formed of a suitable metallic or non-metallic material. In one non-limiting embodiment, aluminum sheet metal may be used as an example. The housing have any suitable configuration depending on the mounting location of the disinfection unit and building structure system (e.g. ceiling, walls, etc.) or type of furniture into which the unit will be incorporated. Accordingly, the housing 101 may be narrower or shorter in various dimensions (i.e. length, width, height) than others. In one embodiment, the housing may have an overall general polygonal shape such as rectilinear, or a non-polygonal shape. An electrical junction box 110 may be provided on or in the housing configured to couple electric power and control wiring cables to the UV-C lamps 108 and fan 109 for controlling operation of the disinfection unit 100.

Figure 2:
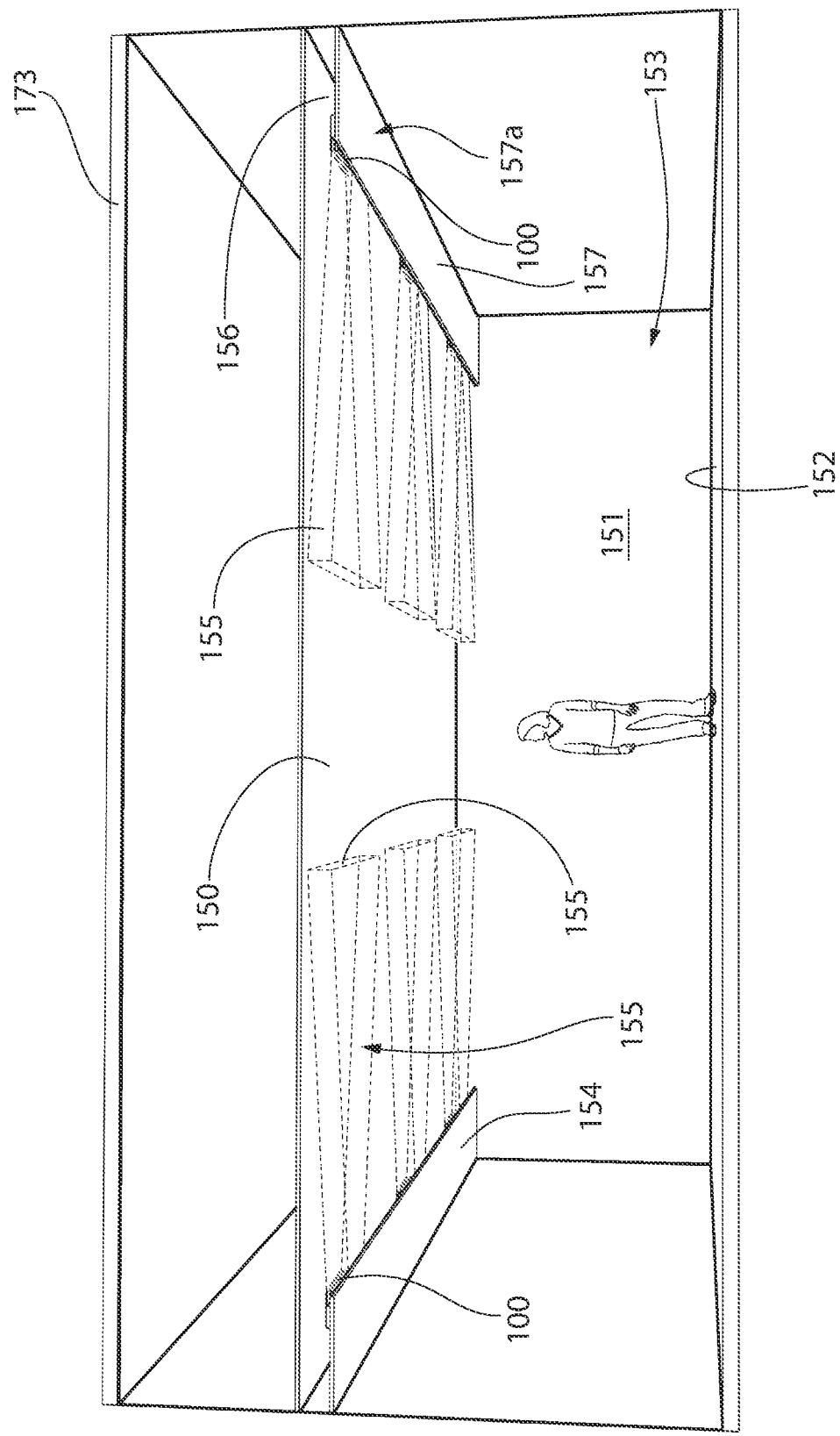
FIG. 2 is a perspective view of a building occupiable space integrating the disinfection unit of FIG. 1 into a perimeter soffit system of the ceiling.

FIG. 2 depicts one embodiment of a UV air purification system incorporating one or more individual UV disinfection units 100 into a perimeter soffit system usable with any type regular or acoustic ceiling system. A drywall grid soffit system, such as those available from Armstrong World Industries of Lancaster, PA, is one non-limiting example of a soffit system which may be used. However, the disinfection units may be incorporated into any type building soffit regardless of materials of construction or soffit configuration.

FIG. 2 illustrates an exemplary occupiable space 153 in a building generally comprising a ceiling 150, walls 151, and floor 152. The soffit system comprises one or more soffits 154 extending perimetrically along the walls proximate to the wall-to-ceiling interface. In the non-limiting illustrated embodiment, each soffit 154 includes an elongated bottom soffit wall 157 which may be horizontally oriented and defines a bottom surface 157a which faces downwards towards the occupiable space. Surface 157a may be planar (shown) or non-planar in other embodiments. The solid soffit wall 157 at least partially and in some cases fully conceals and shields the disinfection unit 100 from view by the building occupants below.

Bottom soffit wall 157 is spaced vertically apart and downwards from the ceiling to define a recess 156. The disinfection units 100 may be mounted within the recesses of the soffits 154 in a spaced apart manner and concealed manner around the perimeter of the room. In the illustrated embodiment, recess 156 is inwardly open on one side allowing room air in space 153 to be drawn into the disinfection units 100. In other possible embodiments, the recess of soffit 154 may be outwardly open facing towards the walls 151. In yet other possible embodiments, soffit 154 may be upwardly open. This latter construction is often used to add accent lighting around the perimeter of the occupiable space which shines onto the ceiling. Soffits 154 may also be open on more than one side to the occupiable space below.

Figure 4:
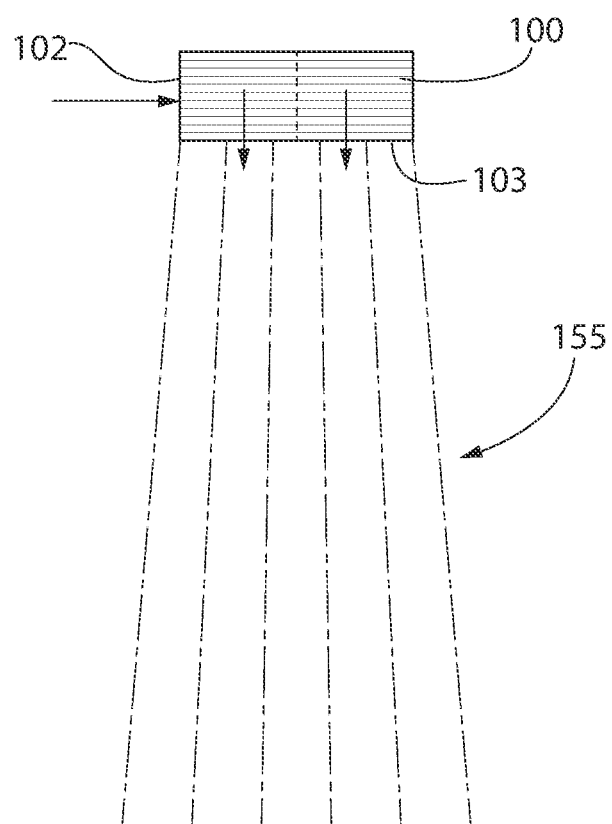
FIG. 4 is a top view of one of the disinfection units of FIGS. 2 and 3 showing the emitted UV light path and airflow discharge flow arrows from the unit.

Soffits 154 may be fixedly coupled to the walls 151 and located around the perimeter of the room or occupiable space as shown in FIG. 2. In other embodiments, the soffits may be spaced inwards from the walls and supported by the ceiling 150 and/or structural members (e.g. T-bar support grid, etc.) which support the ceiling. The soffits may be spaced a short distance from the perimeter defining an outwardly open recess 156 facing the walls. In some embodiments, the soffits may be spaced a substantial distance away from the wall forming a more centrally located fixture near the ceiling. Such an embodiment is shown in FIG. 4 in which the soffit comprises a laterally/horizontally wide and broad bottom soffit wall 157 in the form of a square located in a central portion of the occupiable space 153. Such a soffit configuration is sometimes referred to as a "canopy" in the ceiling system arts. Other polygonal shapes may be used such as hexagonal, pentagonal, star-shaped, or triangular as some non-limiting examples. This soffit wall may alternatively be non-polygonal such as circular, oval, or other arcuately curved shapes.

In one embodiment, as shown in FIG. 2, the soffit 154 is linearly elongated and comprises a linearly extending bottom soffit wall 157 spaced downwards from the ceiling to define the recess. In other embodiments, the soffit may be arcuately curved and comprises an arcuately extending bottom soffit wall 157 spaced downwards from the ceiling to define the recess 156 in which the disinfection units 100 are mounted. In some embodiments, a plurality of elongated straight/linear soffit walls 157 may be arranged substantially parallel to each other extend between opposing walls of the occupiable space forming a ceiling and soffit system in which no two soffit walls intersect each other. In some embodiments, at least some of the soffit walls may be oriented perpendicularly to each other and may intersect at corners of the space. In other possible embodiments, the soffit walls 157 may be elongated and arcuately curved.

Figure 3:
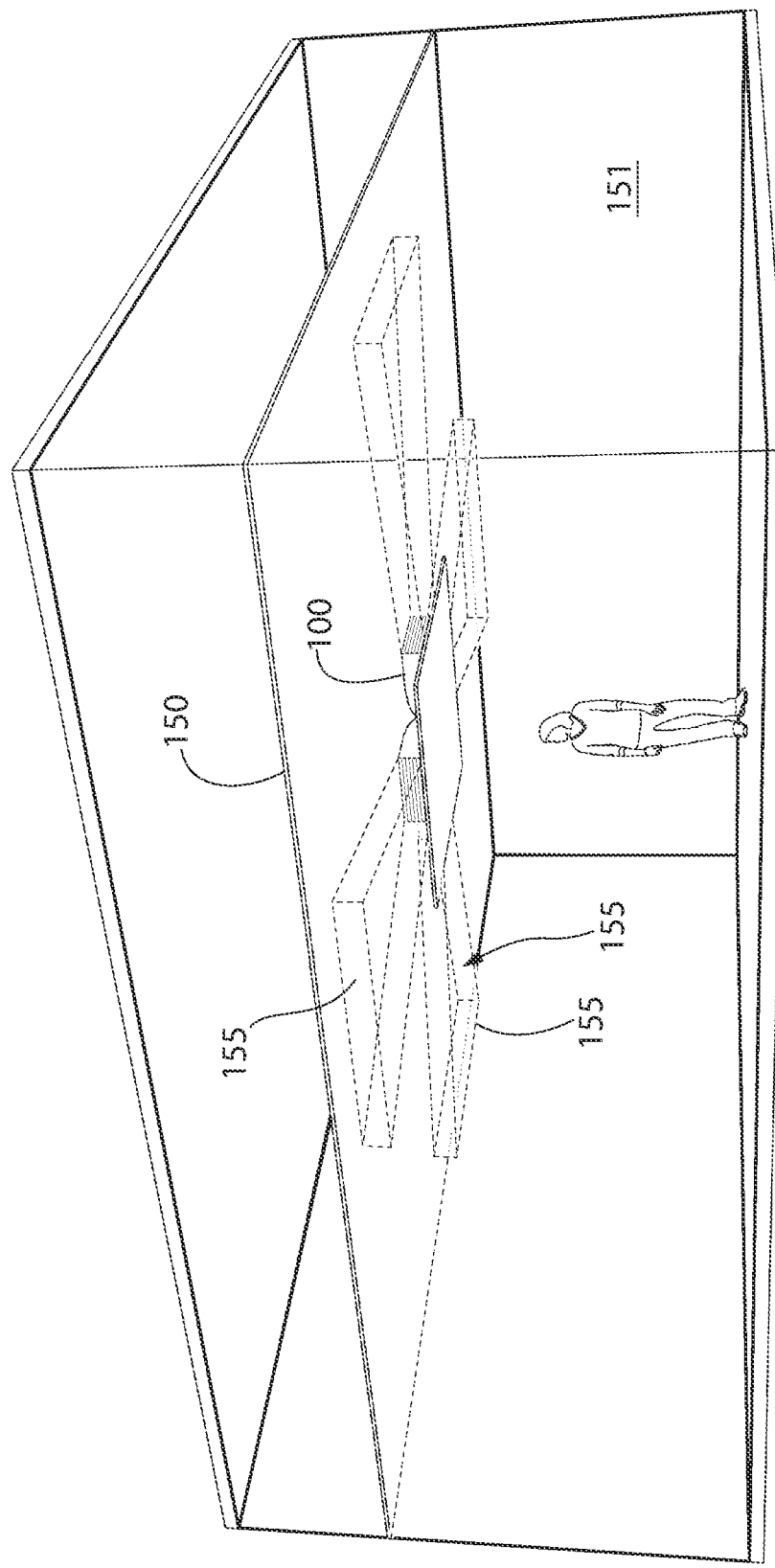
FIG. 3 is a perspective view of a building occupiable space integrating the disinfection unit of FIG. 1 into an interior soffit system of the ceiling in the form of a canopy.

Referring to FIGS. 2-4, the air inlets 102 of each disinfection unit 100 located inside the soffits 154 may be located on one side of the unit housing 101 and the air outlets 103 may face towards the occupiable space. The resultant flow of purified/treated air discharged by the unit and returned to the space is generally represented by the trapezoidal shaped dashed lines in these figures. The UV-C lamps 108 in one embodiment may be fully enclosed by housing 101 of disinfection unit 100 and completely shielded from the room by the housing. In other embodiments, the UV-C lamps 108 may be partially exposed such that the UV light shines outwards from the unit to the occupiable space to simultaneously irradiate the discharge air stream. The light path may also be represented by the dashed lines/boxes in FIGS. 2-4. The discharge air is therefore simultaneously irradiated as it returned by the fan 109 of unit 100 to the space. In this later embodiment, the soffits 154 are configured to completely shield occupants in the occupiable space from direct line of sight to the UV-C lamps 108. Elevation of the disinfection units 100 and UV-C lamps 108 near the ceiling 150 adds a further layer of UV exposure protection.

Figure 5:
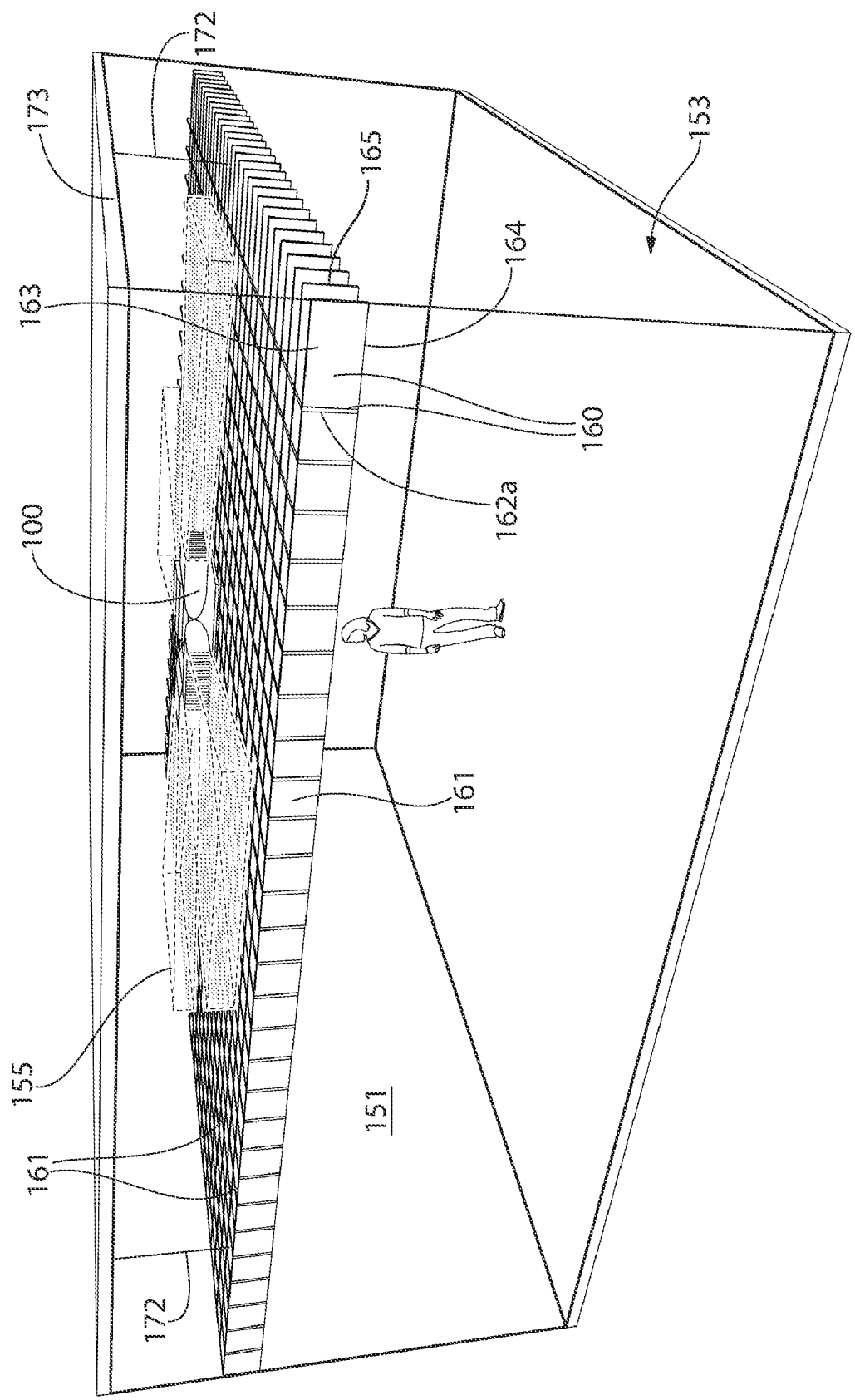
FIG. 5 is a perspective view of a building occupiable space integrating the disinfection unit of FIG. 1 into a first embodiment of a ceiling blade system comprising a honeycomb pattern of blades.
Figure 6:
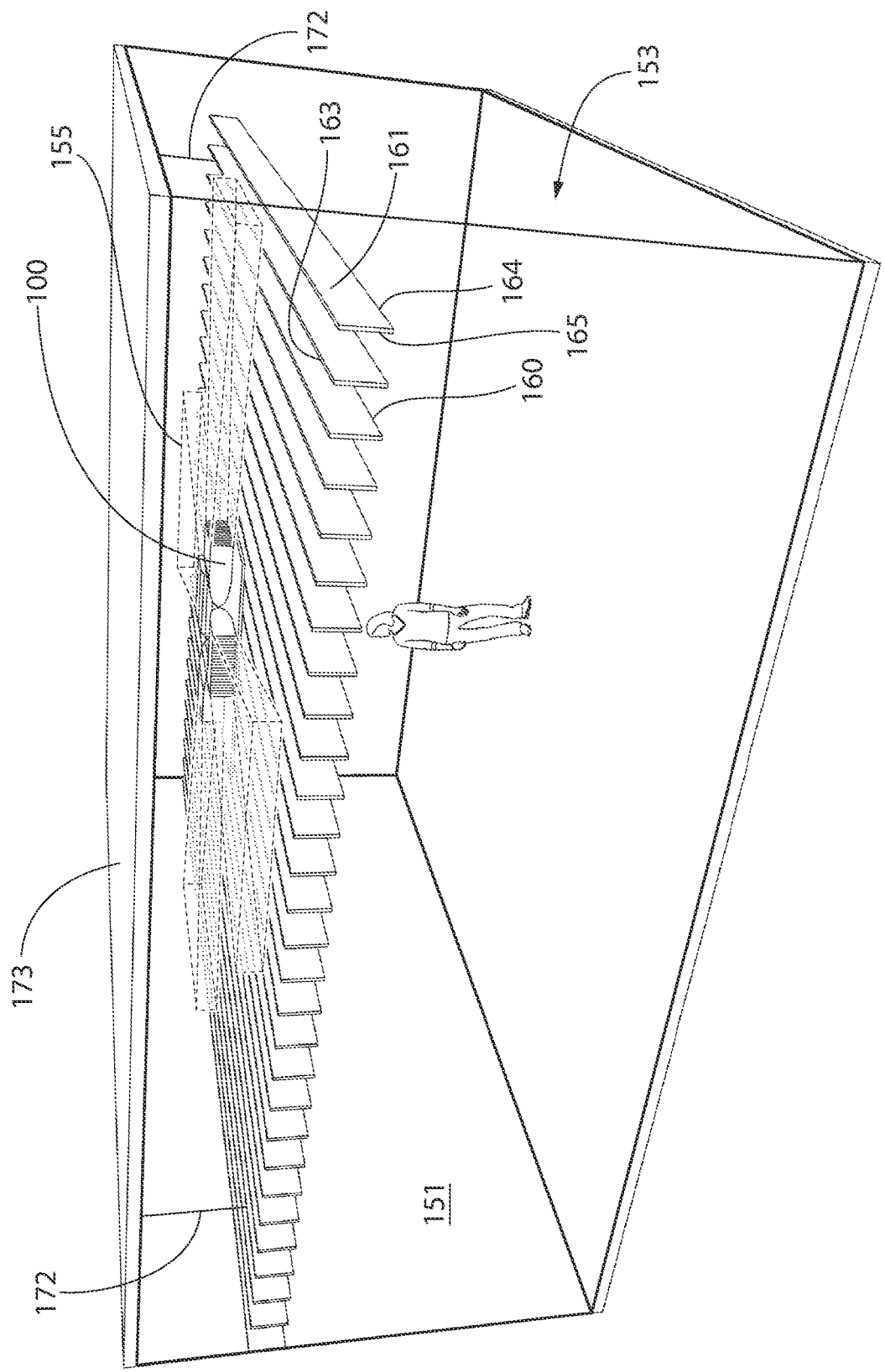
FIG. 6 is a perspective view of a building occupiable space integrating the disinfection unit of FIG. 1 into a second soffit system of a ceiling blade system comprising a linear parallel pattern of blades.

FIGS. 5 and 6 shows the integration of disinfection units 100 into a ceiling system comprising ceiling blades 160. FIG. 5 shows the disinfection units 100 located and mounted above an open "egg crate" or "open cellular" type blade array. The array comprises a plurality of orthogonally intersecting linear and planar blades 160 which create a honeycomb pattern of open cells 162. Cells 162 open downward to the occupiable space 153 and upwards to the headspace between the blades and overhead building support structure 173. The cells may be formed by interlocked slotted blades comprising upwardly and/or downwardly open elongated slots 162a. The array of blades 160 are configured for mounting in a suspended manner from the overhead building support structure 173 via appropriate hanger elements 172, such as for example without limitation fasteners, hangers, wires, cables, rods, struts, etc.

FIG. 6 discloses blades 160 arranged in the pattern of a parallel series of linear planar blades which do not intersect. For either illustrated pattern and layout of acoustic blades, untreated air is drawn upwards from the occupiable space 153 through the blades, and into each disinfection unit 100. Treated air discharged by the units flows back through the blades 160 to the occupiable space.

Blades 160 in FIGS. 5 and 6 are generally planar structures having opposing front and rear major surfaces 161 extending between top and bottom edges 163, 164 and vertical ends 165. Blades 160 may be arranged in numerous other polygonal and non-polygonal patterns and may numerous different individual polygonal and non-polygonal configurations including undulating shapes and arcuately curved shapes. Blades 160 may be formed of numerous material including acoustic sound absorbing materials, mineral fiber and fiberglass, metal, wood, felt, polymers, and others. One non-limiting example of an acoustic material which may be used is non-woven layered and formed polyester felt (e.g. PET-polyethylene terephthalate) fiber panels or others.

Figure 7:
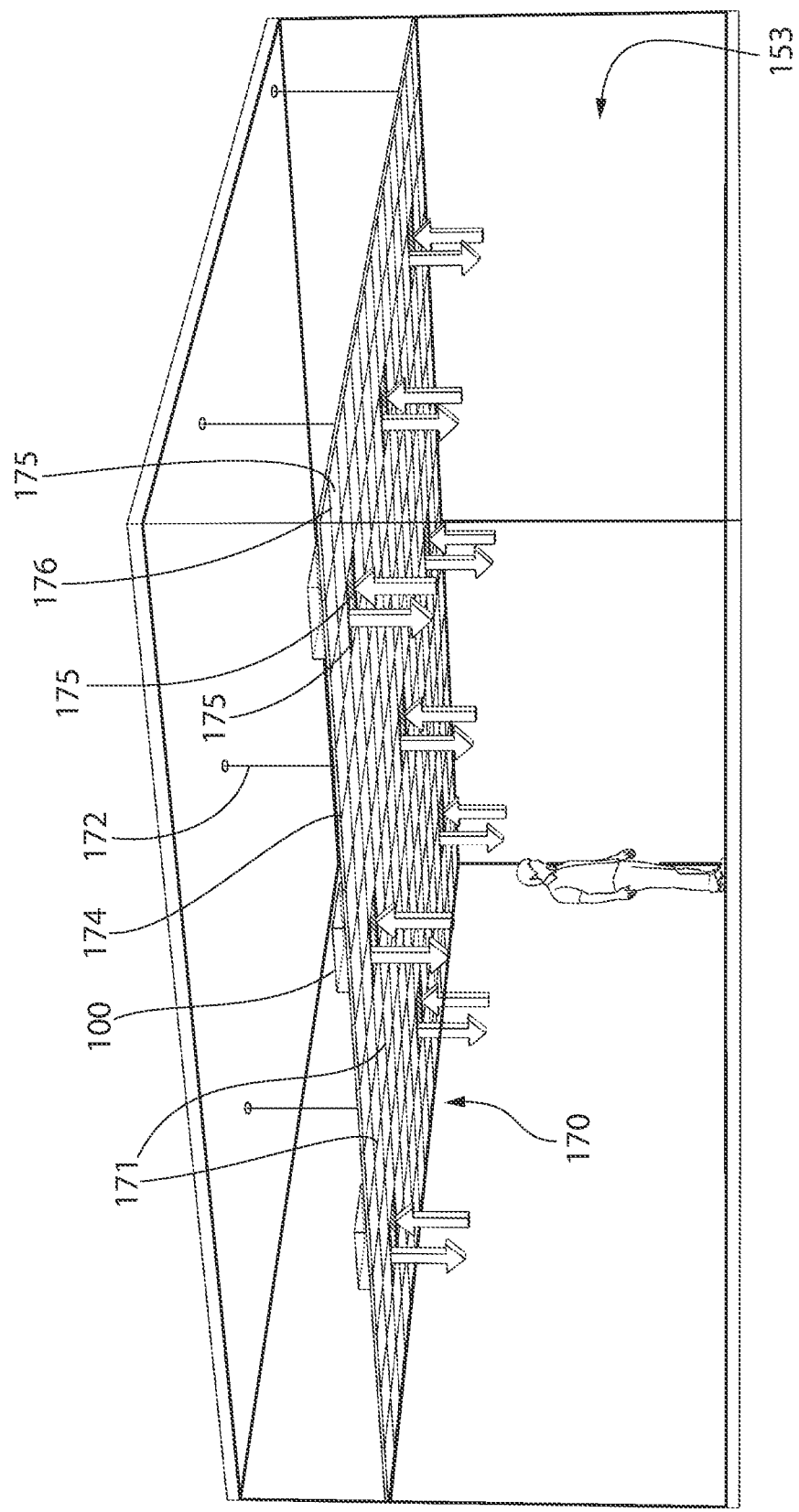
FIG. 7 is a perspective view of a building occupiable space integrating the disinfection unit of FIG. 1 into a first embodiment of a standard grid array type suspended ceiling system.
Figure 8:
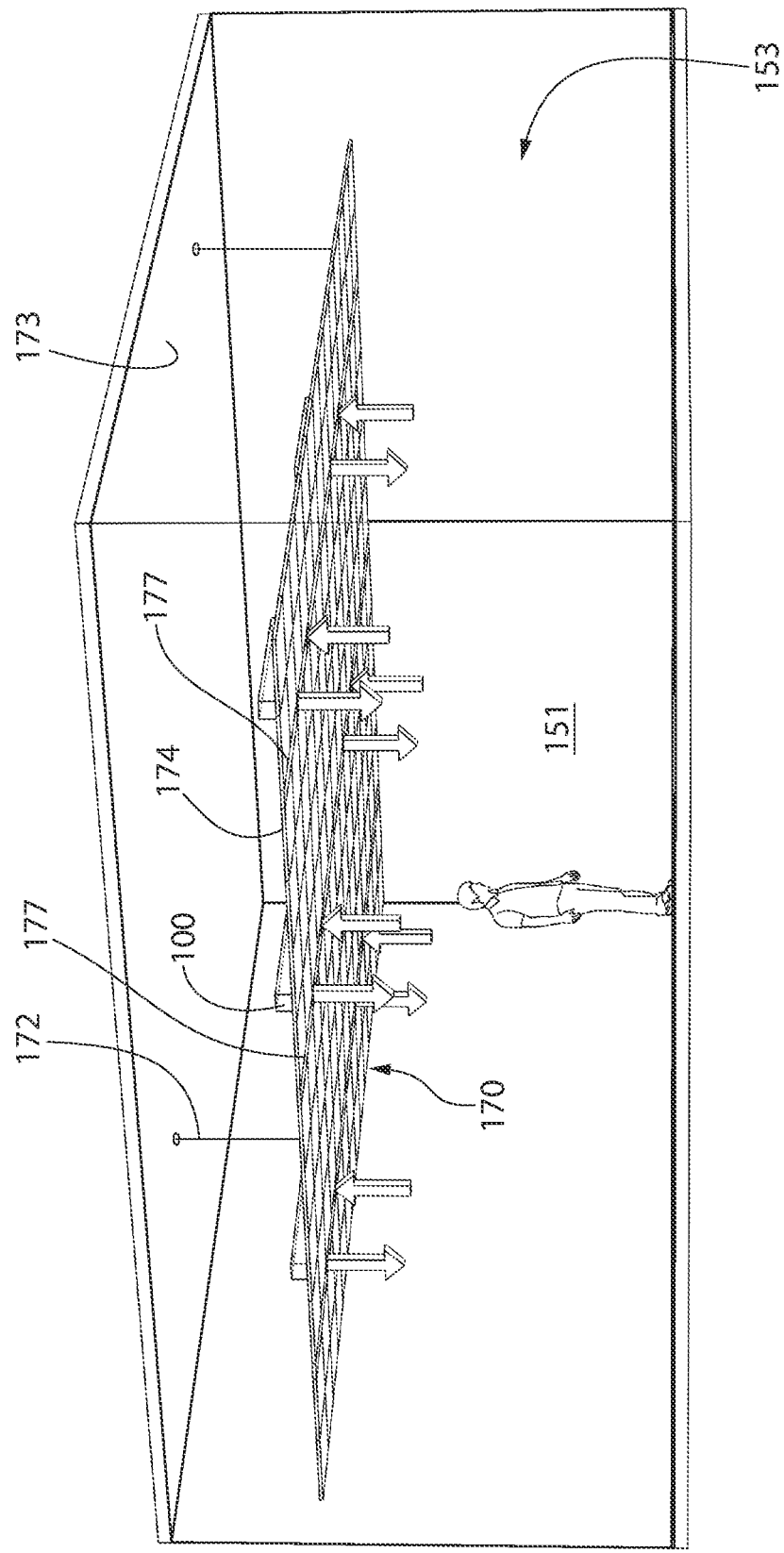
FIG. 8 is a perspective view of a building occupiable space integrating the disinfection unit of FIG. 1 into a second embodiment of a grid array type suspended ceiling system comprising utility slots.

FIGS. 7 and 8 show the integration of disinfection units 100 of the air purification system into a suspended grid ceiling system 170. The ceiling system generally includes an overhead support grid 174 and plurality of ceiling panels 175 located in open grid spaces defined by the grid. Each panel is supported at its peripheral edges by the grid.

The overhead support grid 174 is configured for mounting in a suspended manner from an overhead building support structure 173 via appropriate hanger elements 172, such as for example without limitation fasteners, hangers, wires, cables, rods, struts, etc. Support grid 174 includes a plurality of orthogonally intersecting metal grid support members 171 having an inverted T-shape (in the hung position) or variations thereof in some embodiments. The grid support members 171 comprise main "runners" or "rails" which are maintained in a substantially parallel spaced apart relationship from each other by grid support members in the form of cross tees or braces oriented perpendicularly to the main runners. The cross braces may be T-shaped or have another shape. The combination of mechanically interconnected main runners and cross braces provide strength and lateral stability to the support grid 171.

The main runner and cross bracing grid support members 171 intersect to form an array of grid openings 176 which become essentially closed by ceiling panels 175 when positioned within the openings. In some non-limiting embodiments, the grid support members 171 may be a standard heavy duty 15/16 inch aluminum T-rail having a 15/16 inch grid face, or 9/16 inch T-rail having a narrow 9/16 inch grid face. Other configurations and materials may be used to form the grid support members.

Any suitable acoustic or non-acoustic ceiling panels 175 may be used in the support grid 174. Ceiling panels 175 may have various overall polygonal and non-polygonal shapes (defined by the opposing top and bottom major surfaces when facing those surfaces). Non-limiting examples include without limitation rectilinear (e.g. square comprising four equal length sides or rectangular comprising two opposing long sides/two opposing short sides), triangular, hexagonal, circular, oval, and others and various combinations thereof in a single ceiling system. In the illustrated embodiment, rectilinear ceiling panels are shown as an example.

Ceiling panels 175 may be constructed of any suitable material or combinations of different materials used in the industry. Some non-limiting examples of ceiling panel materials that may be used include, without limitation, mineral fiber board, fiberglass, metals, metal clad non-metallic filled or honeycomb cores, polymers, wood, various composites, combinations thereof, or other. In one embodiment, the panels 175 may be formed of mineral fiber board. Ceiling panels 175 may be acoustic panels in some embodiments with an NRC (noise reduction coefficient of at least about 0.65 in some embodiments. Acoustic mineral fiber panels when used for noise reduction typically have a higher fiberglass or mineral fiber/wool content than non-acoustic panels which provide better sound absorption and blocking. Suitable ceiling panels 100 which may be used are available from Armstrong World Industries of Lancaster, Pennsylvania.

The ceiling panels 175 may have a variety of sizes, thicknesses, and weight. Examples of sizes for rectilinear shaped panels typically used in suspended grid ceiling systems may include without limitation 24 inch×24 inch, 24 inch×48 inches, or other as shipped from the factory (without field cutting/modification to fit building features and room sizes). Panels 100 may have any suitable thickness, such as typically about ¾ inches in some embodiments, or more or less in other embodiments.

Figure 9:
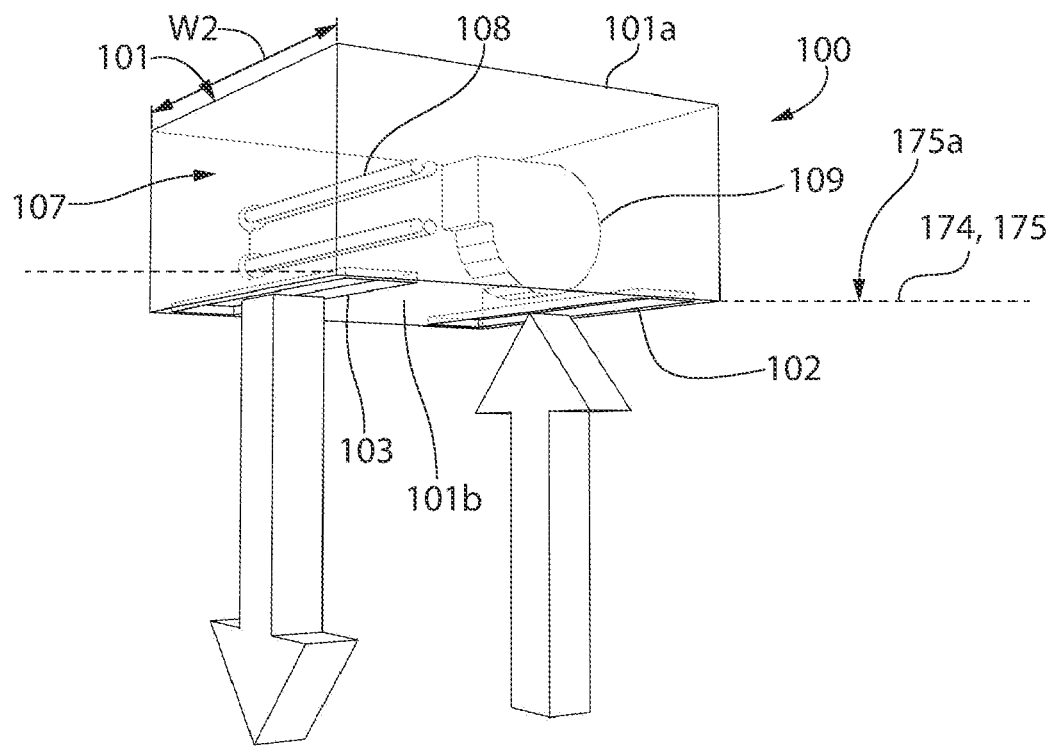
FIG. 9 is a perspective view of a first embodiment of an air purification disinfection unit according to FIG. 1 usable with the ceiling system of FIG. 7.

With continuing reference to FIGS. 7 and 8, disinfection units 100 are mounted above the support grid 174 and ceiling panels 175 therein. FIG. 9 shows a disinfection unit usable in the standard suspended ceiling system 170 of FIG. 7. Openings may be cut into the ceiling panels 175 (i.e. cutouts 178) at opposite sides/ends of the panels to accommodate the air inlet and outlet 102, 103 of the disinfection unit. The housing 101 and the inlet and outlet of disinfection unit 100 in this embodiment may have a width W1 approximately the same as the width of a ceiling panel 175. In other embodiments, width W1 may be less than the ceiling panel. The air inlet 102 and air outlet 103 of each disinfection unit 100 faces downwards towards the occupiable space through the cutouts 178. Accordingly, the air inlet and outlet of the housing 101 of each disinfection unit 100 is located directly above correspondingly shaped cutouts 178 at the opposing ends/sides of the ceiling panel 175 above which the disinfection unit is mounted. In this embodiment, one of the ceiling panels is interposed beneath and between a bottom surface 101b of each disinfection unit and the top surface 178a of that ceiling panel. The top surface 101a of the disinfection unit housing 101 faces upwards in an opposite direction away from the occupiable space. Each disinfection unit 100 is disposed directly adjacent top surface 175a of the ceiling panel and may be supported by the support grid 174 (i.e. grid support members 171) and/or via hangers 172 mounted to the overhead building support structure 173 on which the units may be mounted.

Figure 10:
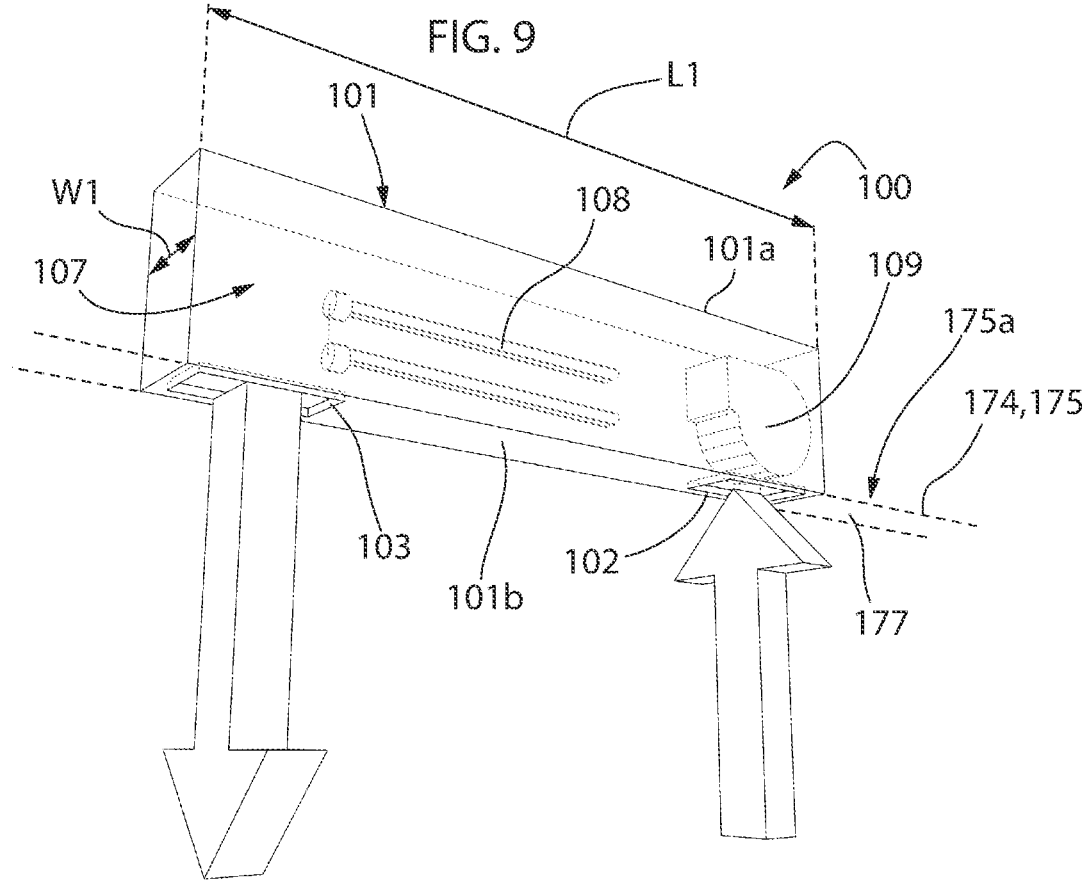
FIG. 10 is a perspective view of a second embodiment of an air purification disinfection unit according to FIG. 1 configured for mounting the utility slots of the ceiling system of FIG. 9.

FIG. 10 shows a narrow profile disinfection unit 100 having a linearly elongated housing 101. This unit may used in TechZone® suspended ceiling systems (available from Armstrong World Industries of Lancaster, Pennsylvania). These ceiling systems integrate and organize utilities such as luminaires/lighting, air diffusers, fire protection sprinkler system components (e.g. sprinkler heads), sounds systems (e.g. speakers), video surveillance equipment, occupancy sensors, or other devices into linearly elongated relatively narrow utility slots 177 formed in the ceiling support grid 174 between the ceiling panels 175. The slots may be formed in suspended ceiling systems by selective spacing and mounting of the grid support members 171 of the support grid 174 previously described herein (e.g. main runners and/or cross-tees) to form continuous narrow openings between ceiling panels. The utility slots are narrower in width than the length or width of the ceiling panels 175. Example widths of the utility slots 177 may be about 4-12 inches; however, other suitable widths may be provided. The utility slots 177 span multiple panels in length generally from approximately one side of or wall 151 the occupiable space to the opposite side or wall. Accordingly, the utility slots extend substantially continuously in structure from one wall 151 of the occupiable space to an opposite wall of the space. Multiple parallel utility slots 177 may be provided in the ceiling system in spaced apart relationship as shown in FIG. 8. The air inlet 102 and outlet 103 of the disinfection unit is linearly elongated as well parallel to the length of the utility slot 177. The disinfection unit housing 101 in FIG. 10 therefore may have a length L1 which is equal to or greater than four times its width W1. Width W1 of the housing may be approximately the same as the width of the utility slot 177. The air inlet and outlet 102, 103 in this embodiment concomitantly has a width about the same as width W1 of the unit as shown.

The air inlet and outlet 102, 103 of each narrow profile disinfection unit is disposed within in the utility slot formed between the grid support members 171 and faces downwards such that each disinfection unit draws air from and discharges air back to the occupiable space through the utility slot 177. In one embodiment, there are no cut pieces of the ceiling panels 175 sized to fit in slot 177 which are interposed between a bottom surface 101b of each narrow profile disinfection unit and the occupiable space below the slot. Instead, the narrow profile unit is located between adjacent panels above the downwardly open utility slot. Each housing 101 of the narrow profile disinfection units is disposed directly within and/or adjacent the top of the utility slot 177 in proximity thereto such that the bottom surface 101b of the unit's housing closes a portion of the slot and is exposed to the occupiable space below. In other embodiments, however, a narrow section of cut ceiling panel may mounted below the unit's housing 101 in utility slot 177 and supported from the grid support members 171 adjoining each longitudinal side the slot. Accordingly, a narrow cut piece of ceiling panel may be interposed between the bottom surface 101b of the disinfection unit housing 101 in slot 177 and the occupiable space below for aesthetic reasons. The narrow profile disinfection units 100 may be supported by the support grid 174 (i.e. grid support members 171) adjacent to the slot 177 and/or hangers 172 from the overhead building support structure 173. It bears noting each of the elongated utility slots 177 which span across multiple ceiling panels 175 may have two or more disinfection units depending on the length of the slots and size of the occupiable space 153

It bears noting that the horizontally elongated narrow profile disinfection unit 100 shown in FIG. 10 for use with the narrow utility slots 177 advantageously provides increased resonance time and exposure of air stream extracted from the occupiable space to the UV-C lamps 108. The linearly elongated tubular UV-C lamps 108 may be oriented parallel to the air flow pathway through the unit as shown to enhance irradiation of the air stream and deactivation of airborne pathogens/microbes suspended therein.

Figure 11:
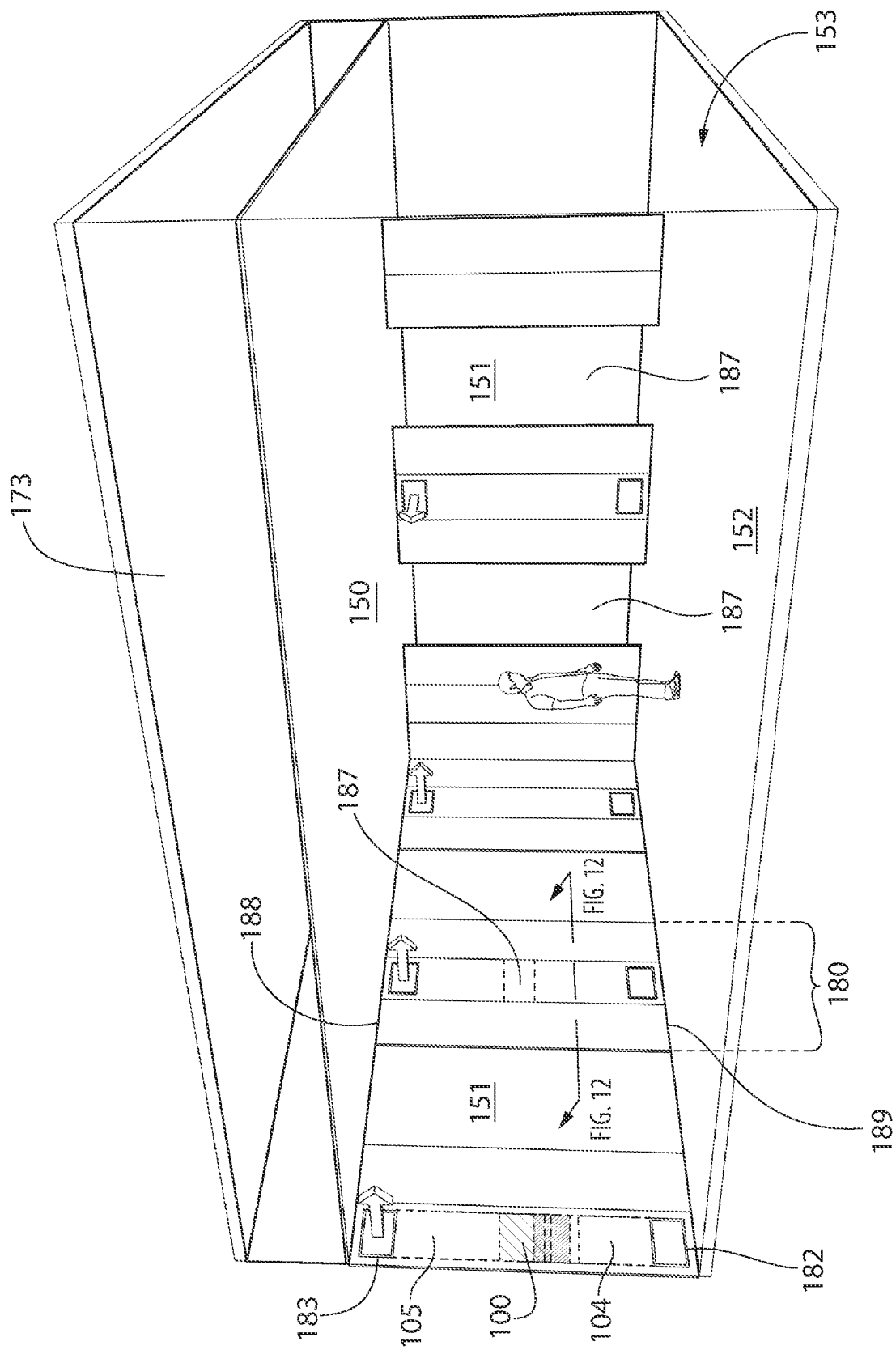
FIG. 11 is a perspective view of a building occupiable space integrating the disinfection unit of FIG. 1 into wall panels mountable to structural wall framing.
Figure 12:
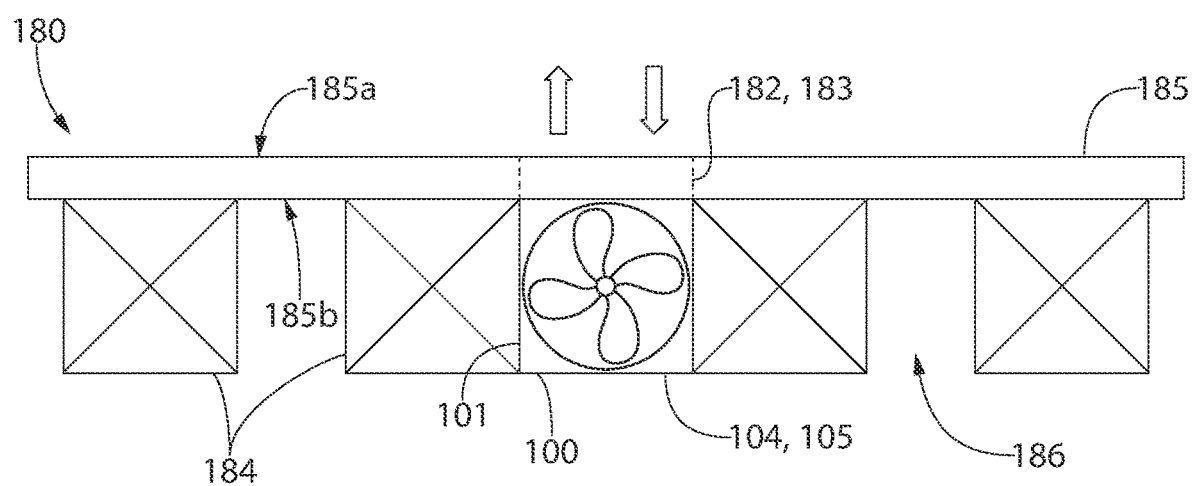
FIG. 12 is a cross-sectional view taken from FIG. 11 of one of the wall panels showing the mounting arrangement of the disinfection unit.

According to another aspect of the disclosure, an air purification wall system is provided. Disinfection units 100 may be integrated into permanent or movable/portable wall systems employed in the occupiable space 153. FIGS. 11 and 12 show a first embodiment comprising pre-fabricated air purification wall panels 180 which are configured for attachment to the permanent structural wall framing of the building at the occupiable space, which may comprise a plurality of vertical structural studs 184 formed typically of wood or metal. The studs define hollow wall cavities 186 between them. Standard 16 inch or 24 on-center spacing, or other spacing may be used with the wall panels 180.

Air purification wall panels 180 have a rigid planar body which may be formed by a vertically elongated sheet-like face frame 185. The face frame defines a solid wall section in one embodiment which extends in height approximately from the floor 152 to ceiling 150. Face frame 185 is configured for erection and use in a vertical orientation in the occupiable space. The face frame may have a width which laterally spans across multiple studs 184 and wall cavities 186 between the studs as best shown in the cross-sectional view of FIG. 12. Wall panel 180 may span across at least two studs 184. The height of wall panels 180 may be greater than their width in some embodiments as depicted in FIG. 11.

Face frame 185 is generally sheet-like in construction and defines a generally planar front side or surface 185a and a rear side or surface 185b. Front surface 185a may have various textures and finishes to provide the desired aesthetics for occupiable space. Face frame 185 may be formed of any suitable material for a wall panels, such as drywall, composite materials (e.g. 2 or more layers of different materials or mixtures of materials), fiberglass, wood, metal, or other. The desired aesthetic appearance of the panels 180 may determine the selection of the material type and panel construction. In any event, the air purification wall panels 180 preferably are rigid in construction.

Disinfection unit 100 may be fixedly mounted in the factory on the rear surface 185b of the wall panel 180 (opposite the front surface 185a facing the occupiable space 153 which may have a decorative finish to match the room interior). Face frame 185 extends laterally beyond the housing 101 of the disinfection unit as shown. The disinfection unit housing 101 may have a narrow profile in depth (i.e. front to rear) to fit within the generally shallow wall cavities 186 which may have a depth of only about 3.5 inches in some embodiments (if standard 2×4 inch studs are used in the wall frame construction). Wall cavity depths may vary depending on the size of the studs in the wall structural framing.

An air inlet grille 182 is provided and located at a lower opening formed through the face frame 185 of wall panel 180 adjacent a bottom end 189 of the panel, and an air outlet grille 183 is provided and located at an upper opening through the face frame adjacent a top end 188 of the panel. With additional reference to FIG. 1, inlet duct 104 extends from the opening inlet grille 182 to the air inlet 102 of the disinfection unit housing 101. Similarly, air outlet duct 105 extends from outlet grille 183 to the air outlet 103 of the housing. The ductwork is fixedly attached to the rear side of the wall panel 180 as well. In sum, this forms a self-supporting wall panel with integrated air purification system.

With continuing reference to FIGS. 11 and 12, one or more prefabricated air purification wall panels 180 may be mounted to the wall studs 184 via fasteners or other preferably removable methods which can provide access to the disinfection units 100 on the rear of the panel face frame 185. In some embodiments, an openable/closeable and latchable access panel (represented schematically by dashed lines in FIG. 11) may optionally be furnished in wall panel 180 to provide ready access to the disinfection unit for maintenance on the UV-C lamps, fan, and/or air filters which may be used as previously described herein. The air filters may include high-efficiency air filters such as MERV (Minimum Efficiency Reporting Values) filters, electrostatic charged/enhanced particle filters, HEPA (high efficiency particulate air), true HEPA and HEPA-like filters, ULPA (ultra-low particulate air) filters or similar may be used to reduce airborne pathogens.

The active wall panels 180 may be laterally spaced apart around the perimeter of the occupiable space as shown in one arrangement Standard wall finish materials such passive filler panels 187 formed of drywall or other suitable filler panel room finish materials are used to fill and enclose the open wall cavities 186 between the air purification wall panels 180 to complete the installation. In some embodiments, the filler panels and air purification wall panels may have the same appearance and finish as to be almost indistinguishable with except of the inlet and outlet grilles in the latter. Accordingly, the face frame 185 of wall panels 180 in such embodiments may be formed of the same material (e.g. drywall panels, etc.) and have the same construction as the filler panels 187. In other embodiments, an entire section of wall may be fitted with multiple active wall panels 180 arranged in laterally abutting relationship (there being no gaps between the active wall panels). In other arrangements, two ore more wall panels 180 which may not be sufficient in lateral extent to fill an entire wall may be used in abutting relationship. In yet other arrangements with respect to primarily exterior walls, open spaces or wall cavities 186 between laterally spaced apart may be fitted with and filled by windows.

In operation, untreated room air is drawn inwards into the disinfection unit 100 via the air inlet grille 182, inlet duct 104, and housing inlet 102 by fan 109. The air may pass through upstream air filter 106 (coarse particle filtration or high-efficiency MERV and HEPA type filters as previously described herein), and is irradiated/disinfected by the UV-C lamps 108 (see also FIG. 1). The treated purified air is then discharged from the unit and returned to the occupiable space via the air outlet 103, outlet duct 105, and outlet grille 183. The inlet and outlet grilles may have openings formed by louvers or other decorative features.

It bears noting that the air purification wall system described above may integrate the air purification wall panels 180 into exterior and/or interior structural wall framing of the building. Accordingly, use of panels 180 is not limited to exterior walls.

Figure 13:
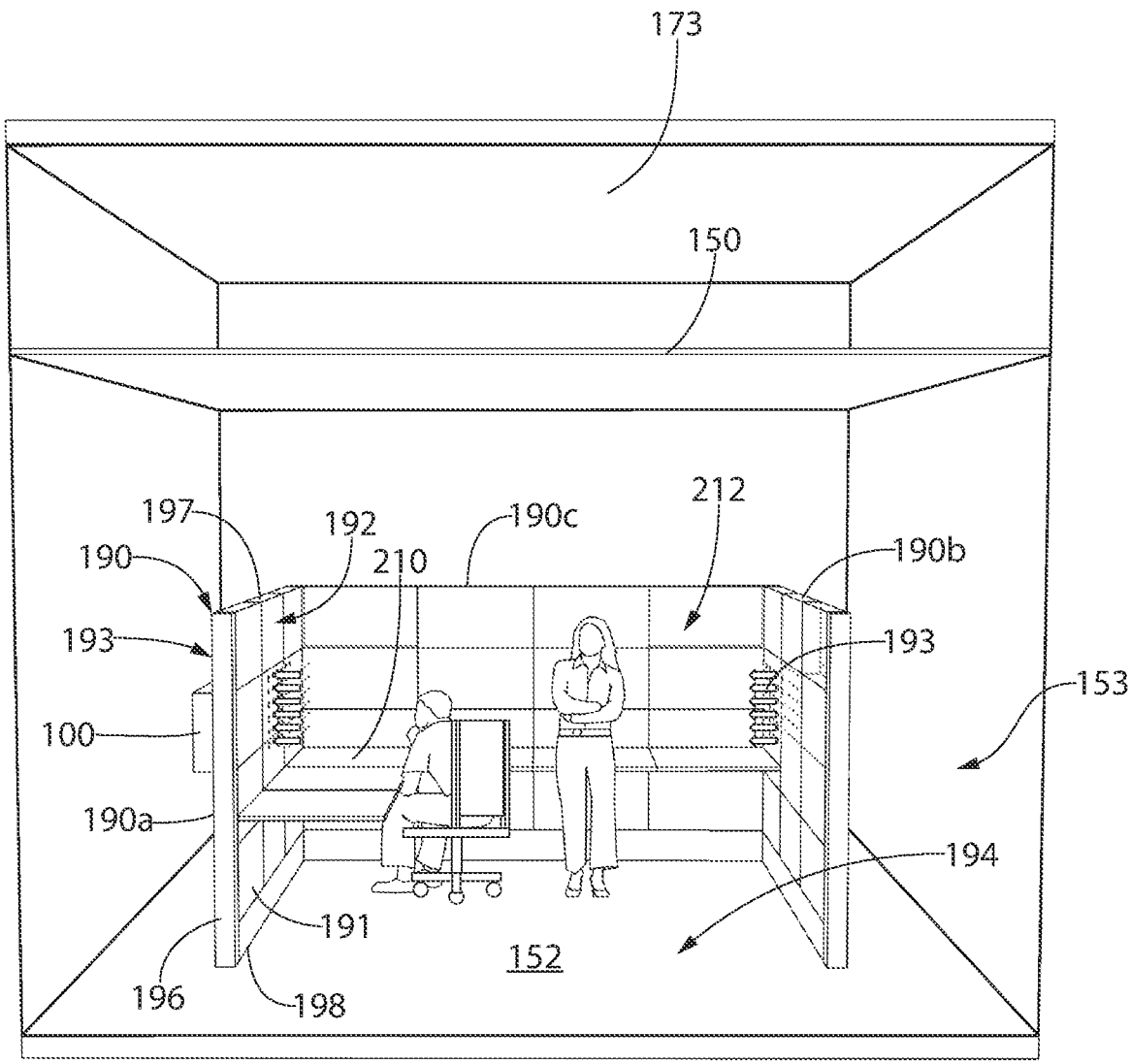
FIG. 13 is a perspective view of a building occupiable space integrating the disinfection unit of FIG. 1 into partition panels of a furniture system used to construct free standing workspace cubicles.
Figure 14A:
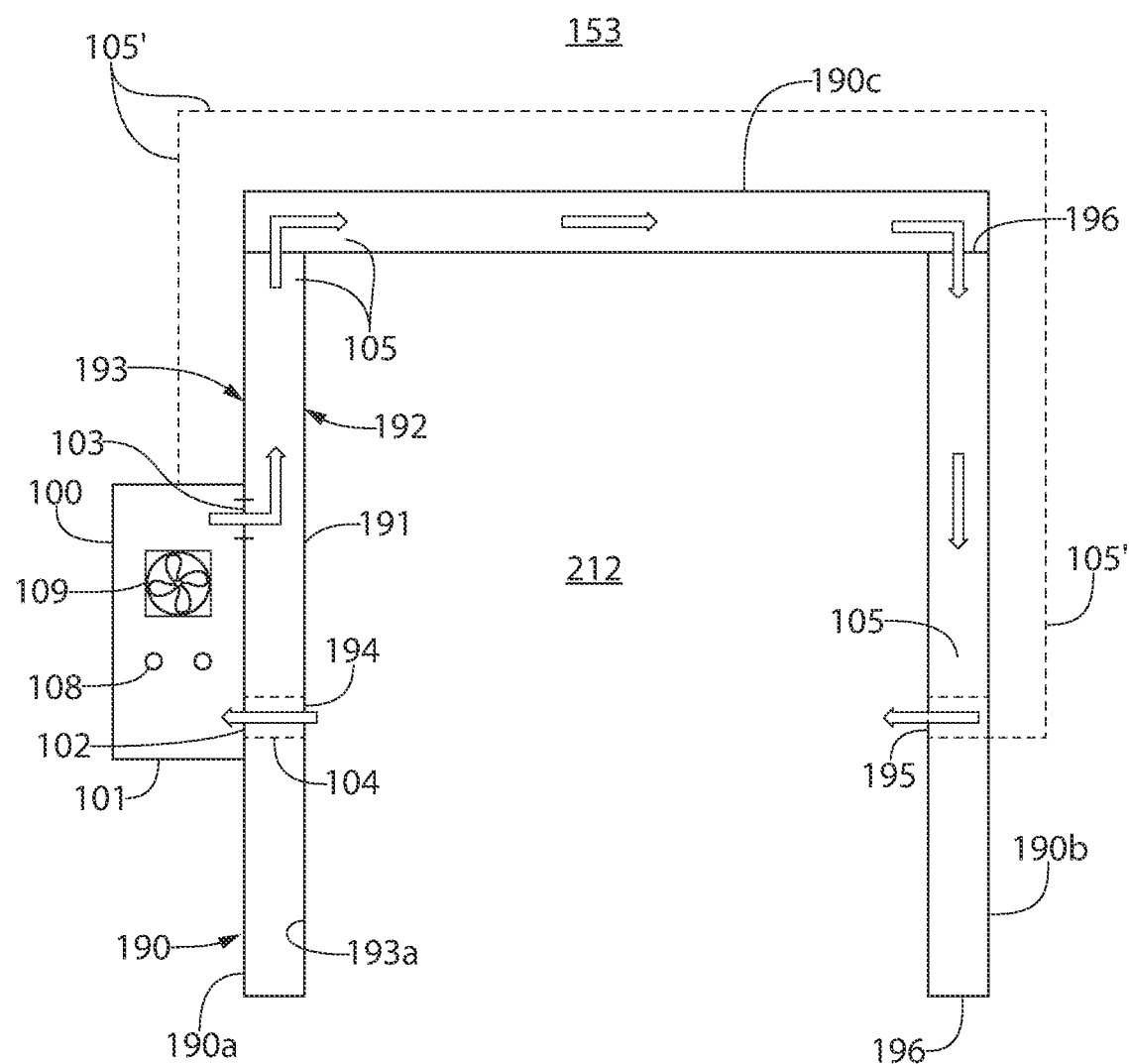
FIG. 14A is a top view schematic diagram of a first embodiment of a cubicle based air purification system of FIG. 13.
Figure 14B:
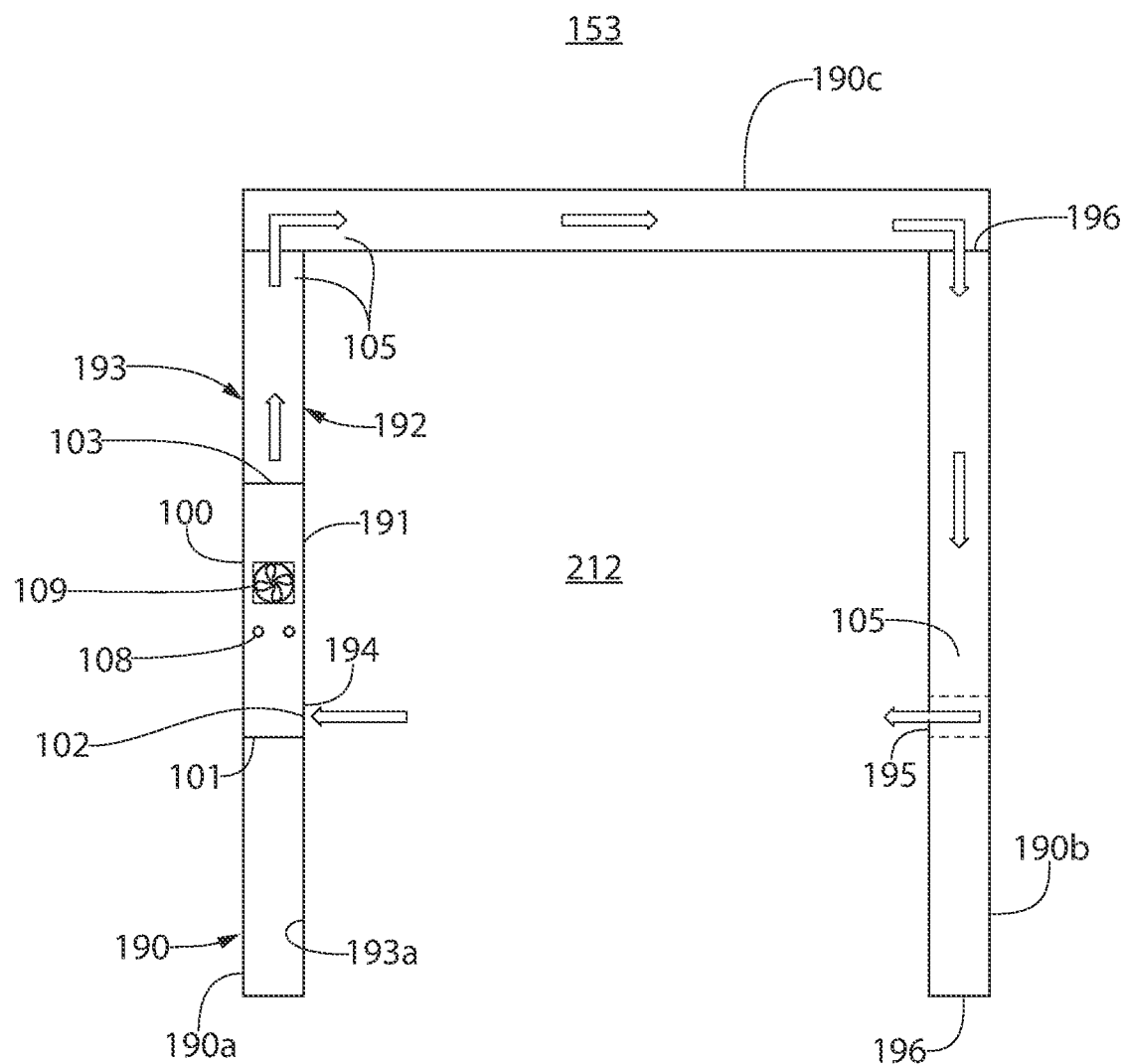
FIG. 14B is a top view schematic diagram of a second embodiment of a cubicle based air purification system of FIG. 13.

FIGS. 13 and 14A-B depict a an air purification panel-based system, but one in which the panels are configured to form an interior air purification partition system integrated into a furniture system. Multiple wall panels configured as partition panels are assembled and mechanically coupled together to create self-supporting and free standing workspace cubicles 212 within the interior of the occupiable space 153 spaced away from perimeter structural wall framing of the space. Cubicle 212 is a volumetric work area defined by a plurality of panels 190 comprising partition panel 190a, partition panel 190b opposite and oriented parallel to panel 190a, and intermediate partition panel 190c extending between and perpendicularly to partition panels 190a and 190b. Each partition panel 190 is planar and defined by a sheet-like partition frame 191 of thickness comprising a front side or surface 192 facing inwards and opposing rear side or surface 193 facing outwards from the cubicle 212. An interior cavity 193a is defined between the front and rear surfaces which may be filled with sound absorbing insulation or materials for noise control. Any suitable commercially-available sound absorbing material may be used. Each panel 190 includes opposing vertical sides 196 extending between a top 197 and bottom 198 of the panel.

Partition panels 190 (e.g. panels 190a, 190b, and 190c in this non-limiting example) are movable and coupleable together. Each panel is a self-supporting and may be free-standing unit on its own, whereas the foregoing wall panels 180 require securement to the structural wall framing of the occupiable space for support as previously described herein. The partition panels 190 (partition frames 191) each have a height as shown substantially less than the height between the floor 152 and a ceiling 150 of the occupiable space 153. At least a 12 inch or more gap therefore may be formed between tops 197 of the partition panels 190 and ceiling 150 in some exemplary constructions.

Each cubicle 212 may comprise its own dedicated air purification disinfection unit 100 to remove airborne pathogens from within the volume defined within the cubicle partitions. Disinfection unit 100 in some non-limiting embodiments may be mounted to the rear surface 193 of the partition panel 190 opposite the cubicle work area (e.g. panel 190a in the illustrated example). This arrangement is shown in FIG. 14A. In other embodiments, disinfection unit 100 may be completely concealed and mounted within the partition panel 190 between the front and rear surfaces 192, 193. This internal mounting arrangement is shown in FIG. 14B. A minimum panel thickness of approximately 4 inches may be sufficient for internally mounting disinfection unit 100 in the panel. The internal disinfection unit mounting arrangement is beneficial where multiple cubicles 212 are to be constructed by sharing and/or abutting partition panels 190.

Air inlet duct 104 extends perpendicularly through panel 190a from inlet grille 194 in front surface 192 through rear surface 193 to air inlet 102 of the disinfection unit. Grille 194 may be similar to inlet grille 182 in construction or different. An outlet grille 195 is located in partition panel 190b opposite partition panel 190a. Grilles 194, 195 may be similar to inlet and outlet grilles 182, 183 previously described herein in construction or different. The grilles 194, 195 may be located above horizontal work surface 210 in cubicle 212 to circulate purified air past the users face for obvious performance and health benefits.

In one arrangement, air outlet duct 105 may be routed internally through partition panels 190a, 190b, 190c within panel cavities 193 from air outlet 103 of disinfection unit 100 to outlet grille 195 in panel 190c. In another alternative arrangement, outlet duct 105' may be routed externally along panels 190a, 190b, 190c on the rear surfaces 193 of the panels. External air outlet duct 105' is represented by dashed lines in FIG. 14. In either of the foregoing mounting positions of the outlet duct, the duct arrangement is configured to circulate air purified by the disinfection unit 100 via fan 109 in a single airflow direction and pathway through the cubicle between the air outlet grille 195 and the air inlet grille 194. This one-way flow may be referred to as "plug flow" in the art and advantageously optimizes air purification performance as there is no mixing of unpurified/untreated and purified/treated air flowing past each other. An air exchange within the cubicle is effected efficiently from one side of the workspace to the opposite side. This is a preferred air flow pathway since purified air is blown past the occupant's face and any respiratory droplets which might contain microbes are immediately drawn into the partition panel mounted disinfection unit 100 on the opposite side of the occupant.

Figure 15:
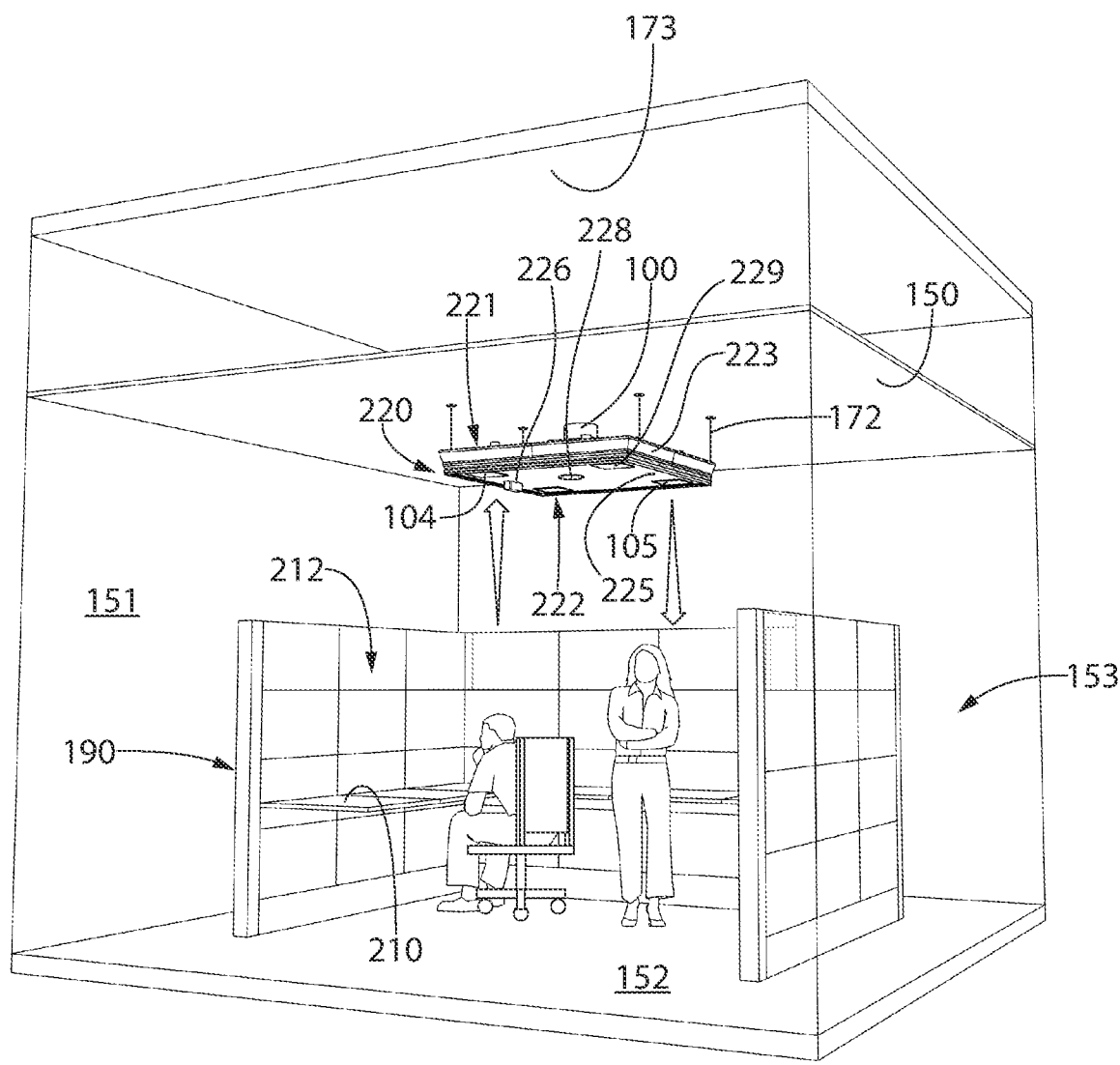
FIG. 15 is a perspective view of a building occupiable space integrating the disinfection unit of FIG. 1 into a canopy suspended from the ceiling over a workspace cubicle.

FIG. 15 depicts a Personal Environment Ceiling System (PECS) comprising a canopy unit 220 which may incorporate a UV-based air purification system in addition to other environmental control utilities. Such utilities may include without limitation task/room lighting 228, heating/cooling with air circulation (HVAC 229), sound and sound masking, UV surface sterilization lamps (see, e.g. FIG. 16), and occupancy sensing. The occupancy sensing (e.g. sensor 225) is operably coupled to a programmable controller 226 incorporated into the canopy unit and may control all aspects of the air purification system and foregoing unities. Occupancy sensor 225 may be any commercially-available type sensor operable to detect motion and/or presence of personnel in an area. Some non-limiting examples include motion sensor, infrared sensors, WiFi/Bluetooth near-field detection sensor, camera-based image sensors, ultrasonic, microwave, etc. Sensor 225 may further be operable to detect the number of occupants within its field of view. An example of the latter type sensor is Philips Lumimotion available from Philips Corporation.

Canopy unit 220 provides a separate self-contained and self-supported work or residential environment control device configured to control all aspects of the environment in the occupiable space under the control of the canopy unit. Canopy unit 220 may be mounted to the ceiling 150 above the occupiable space and supported in a spaced apart manner from ceiling 150 in some embodiments via suitable hangers 172 similar to those previously described herein, or other support mechanisms. FIG. 15 depicts a canopy unit 220 mounted above a cubicle 212 to control the workspace environment therein. In lieu of integrating the disinfection unit 100 into the partition panels 190 of the cubicle as previously described herein, the disinfection unit 100 is supported (e.g. suspended or hung) from the ceiling directly above the cubicle 212. Each cubicle may have a dedicated canopy unit. When the control system (occupancy sensor 225 and controller 226) detects the absence of a person or persons in the cubicle for a preprogrammed period of time, operation of the disinfection unit 100 and other utilities may be terminated to save power. If the canopy unit 220 is equipped with UV surface sterilization (e.g. UV-C lamps 108a further described below), the sterilization system however may not be activated until the occupancy sensor detects the absence of personnel within the cubicle and field of view of the sensor. When the presence of a person(s) is detected, the sterilization system is immediately deactivated by the controller 226. When the cubicle is occupied, the occupancy sensor 225 can detect the number of persons within the cubicle and adjust the HVAC and air purification system as needed based on the number of persons present to optimize efficiency, comfort, and personnel protection.

The frame of canopy unit 220 may be any three-dimensional polygonal or non-polygonal shape (e.g. rectangular or square cuboid, cylindrical, etc.) comprising a top 221, bottom 222 facing the cubicle, and peripheral sides 223 defining a perimeter of the canopy. Disinfection unit 100 may be mounted on the top of the canopy unit as shown in a suitable position to at least partially conceal it from view below, such as approximately centrally located. Inlet and outlets ducts 104, 105 may penetrate the bottom 222 of the canopy unit 220 to draw in air upwards from the cubicle and return purified air downwards thereto as shown (see directional air flow arrows). In other embodiments, untreated air from the occupiable space 153 may enter the air inlet 102 of disinfection unit from around the side of and above the canopy unit 220 rather than through the bottom of the canopy. Either arrangement creates a vertical air circulation pattern in contrast to the horizontal air circulation pattern established with the panel-based disinfection unit 100 system previously described herein in FIGS. 13 and 14. A plurality of canopy units may be provided and spaced apart in the occupiable space 153 to divide the space into a plurality of treatment zones centered around each canopy unit.

Figure 16:
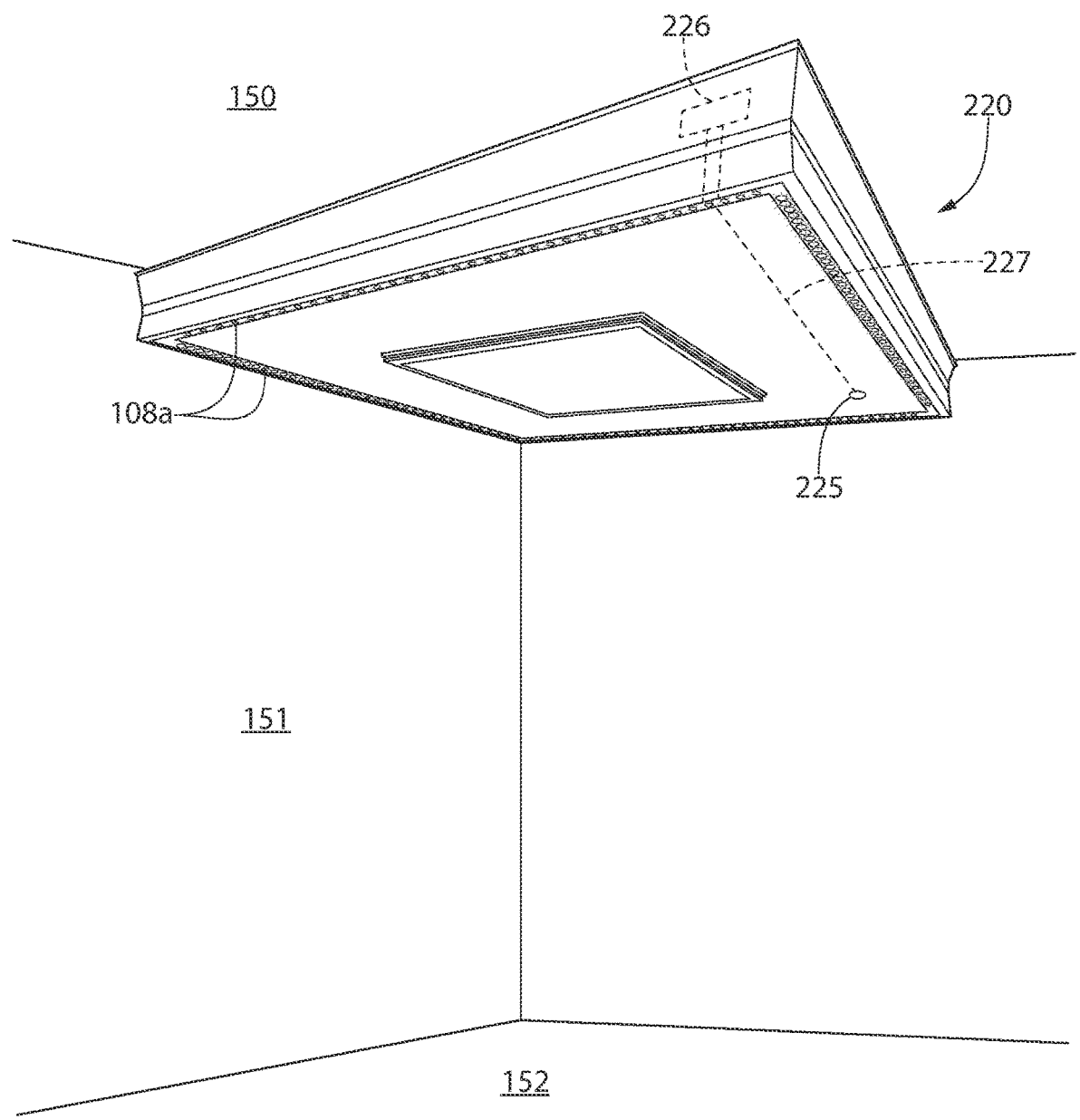
FIG. 16 is a perspective view of a building occupiable space comprising a canopy suspended from the ceiling including a surface sterilization system comprising a plurality of UV ultraviolet sterilization lamp units for disinfection of surfaces within the space.

With additional reference to FIG. 16, canopy unit 220 in some embodiments may further comprise a plurality of downward directed ultraviolet surface sterilization lamp units 108a (other utilities not shown in this figure for clarity). These lamp units may employ UV-C light and are configured to irradiate vertical, angled, and horizontal surfaces within the occupiable space 153 that lie in the line of sight of the lamp units to destroy pathogen/microbe deposits thereon. Horizontal surfaces in the occupiable space where respiratory droplets may fall out of suspension from the air and which are touched frequently by occupants pose the arguably greatest threat of surface contamination and related disease transmission. Non-limiting examples of such horizontal surfaces may comprise floors 152 formed of various fibrous or hard types of flooring materials, hard work surfaces 210 (e.g. horizontal desk/work table areas), or others (e.g. counters, tables, etc.) located within the workspace including but not limited to within cubicle 212 beneath the canopy.

In some embodiments, as shown, the lamp units 108a may each comprise linearly elongated fixtures arranged in linear arrays or strips on the bottom of the canopy. In other embodiments, depending on the spread and saturation of light needed to irradiate and disinfect the surfaces based on their location and surface area, arrays of lamp units arranged in multiple rows and polygonal patterns (e.g. rectilinear 2×2 array, 3×3 array, 3×6 array, etc.) or non-polygonal patterns (e.g. circular, oval, etc.) may be used. In some embodiments, the lamp units may comprise circular disk-shaped lamp housings. The pattern and arrangement of lamp unit arrays and shape of the lamp units does not limit the invention and may be selected to suit such considerations as for example surface decontamination requirements and layout, existing furniture and room configurations, and aesthetics to name a few.

To avoid exposing occupants in the space 153 from direct UV exposure which may have detrimental health effects, the canopy unit in some embodiments includes programmable controller 226 (previously noted herein) operably coupled to the sterilization lamp units 108a via wired or wireless communication/control links 227. Occupancy sensor 225, which may be mounted on the bottom of the canopy unit 220, is operably coupled to the controller via control links 227. The controller is configured via programming instructions or code (software control logic steps) to prevent operation of the sterilization lamp units when the occupancy sensor detects motion in the occupiable space 153. In some embodiments, a timer delay circuit may be provided in either hardware, firmware, or software associated with controller 226 which prevents the sterilization lamps 108a from activating within a preprogrammed delay time period after the occupancy sensor 225 fails to detect movement within its field of view. Once movement is again detected, controller 266 deactivates the lamps 108a.

The controller 226 may be any commercially-available type programmable controller, microprocessor, or microcontroller configured with one or more CPUs (processors), memory (RAM, ROM, etc.), input/output peripherals such as a communications interface circuit or module (wired and/or wireless), etc. as is standardly provided with such devices to provide a fully functional control system.

The canopy units 220 with UV sterilization lamp provisions may be mounted above workspace cubicles 212 if used in the workplace, above desk areas if not, and/or throughout the occupiable space in other areas where such hard surface work surface sterilization might be beneficial such as in reception areas, staging areas, lounging/waiting areas, etc.

Figure 17:
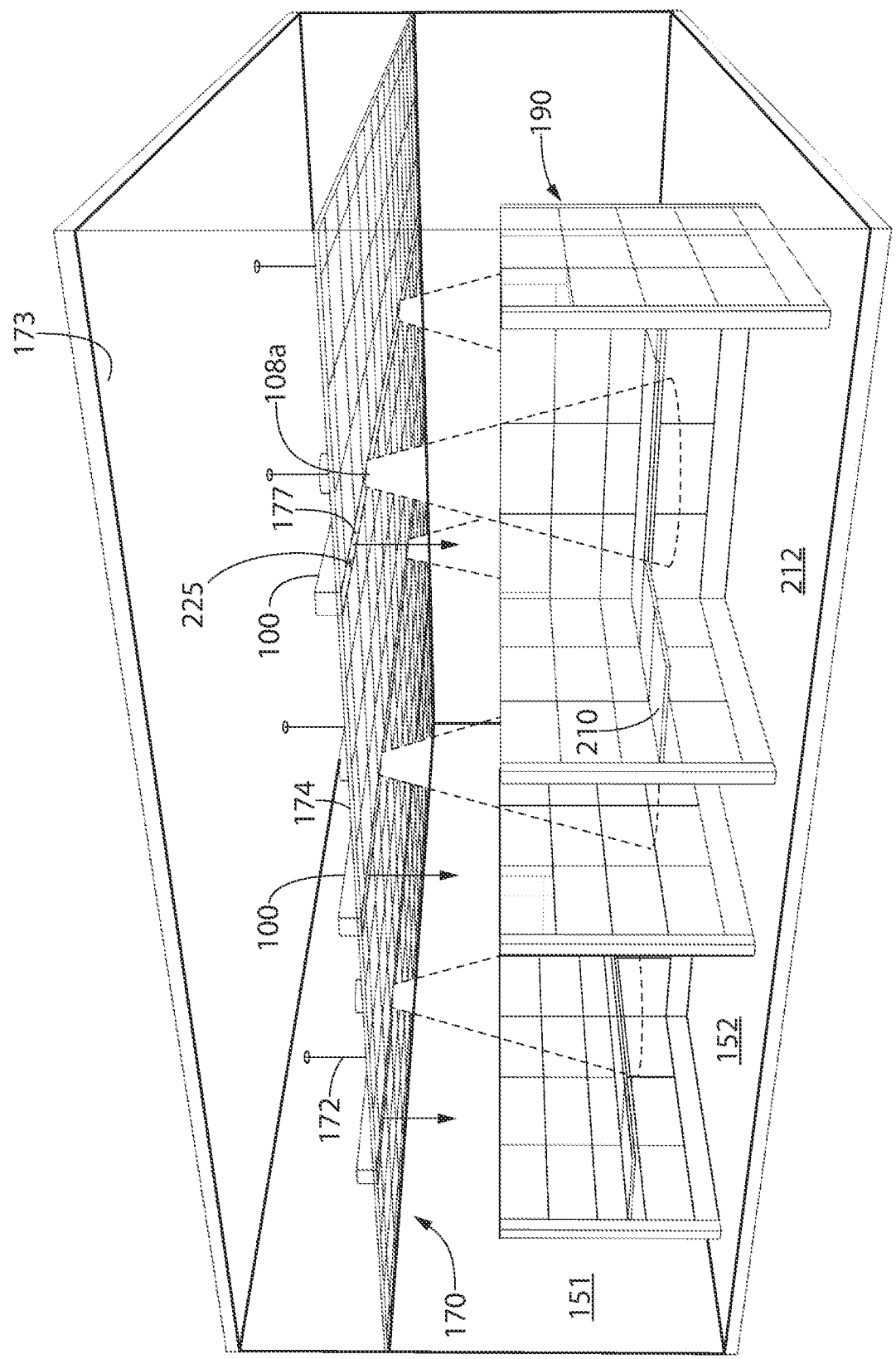
FIG. 17 is a perspective view of a building occupiable space comprising integration of UV ultraviolet sterilization lamp units into the ceiling system above workspace cubicles for disinfection of surfaces therein.

FIG. 17 depicts integration of the downward directed ultraviolet surface sterilization lamp units 108a (e.g. UV-C) into a TechZone® suspended ceiling systems (available from Armstrong World Industries of Lancaster, Pennsylvania) previously described herein with reference to FIG. 8. The lamp units 108a are mounted within the narrow utility slots 177 formed in the ceiling support grid 174 amongst the ceiling panels 175 above workspace cubicles 212 formed by partition panels 190 previously described herein to sterilize vertical and angled surfaces, and horizontal work surfaces 210 in each work area. The inlet and outlet ducts 104, 105 and disinfection units 100 of FIG. 1 are incorporated into the utility slot structures as shown in this figure (applicable to FIG. 8 as well). The light will spread in a generally cone-shaped illumination pattern illustrated by the dashed lines in FIG. 17. The lamp units may be used in other areas beyond the cubicles which contain hard work surfaces that would benefit from periodic sterilization.

Figure 18:
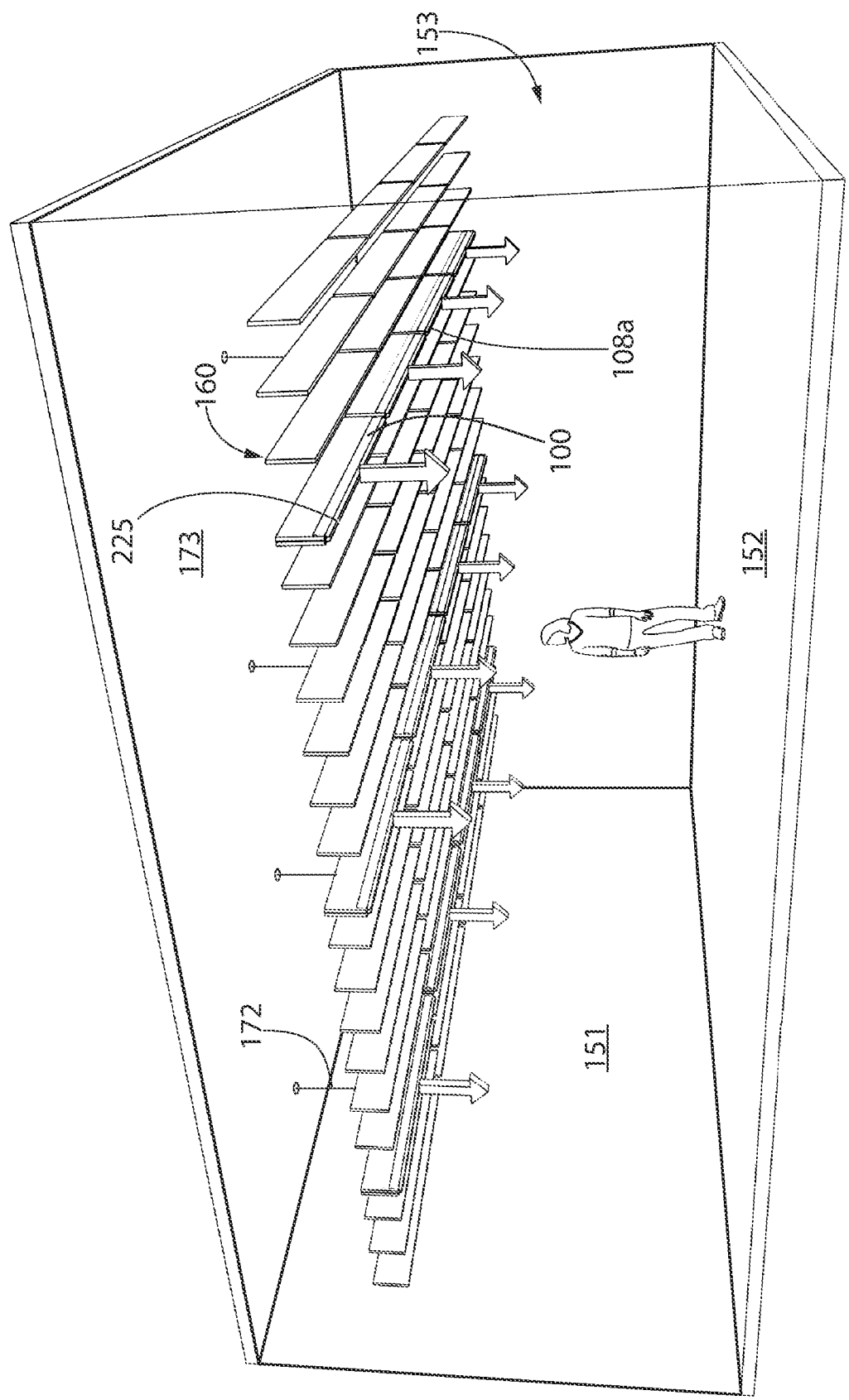
FIG. 18 is a perspective view of a building occupiable space comprising integration of UV ultraviolet sterilization lamp units into a blade ceiling system.

FIG. 18 depicts integration of the ultraviolet surface sterilization lamp units 108a and air purification UV disinfection units 100 into select blades 160 of the blade ceiling system generally disclosed in FIGS. 5 and 6. The UV-C lamp units 108a may be mounted on the bottom edges 164 of blades 160. Not every blade will require lamp units since the light will spread in a generally cone-shaped illumination pattern illustrated by the dashed lines in FIG. 17. The lamp units may also be selectively mounted to blades of either the parallel linear or honeycomb patterned blade arrays previously described herein in locations above and proximate to the work surfaces which require sterilization.

In any of the foregoing ultraviolet surface sterilization embodiments, the UV-C lamp units 108a may be integrated in a discrete and aesthetically pleasing manner via fully or partially flush mounting adjacent to or at the bottom edges 164 of the blades into which they are incorporated. Narrow profile disinfection units 100 as shown in FIG. 10 may be incorporated into the body of some of the blades 160 as needed to adequately purify the volume of air in the occupiable space. Operation of the lamp units and the disinfection units 100 may also be controlled by programmable controller 226 and occupancy sensor 225 of the control system previously described herein. The blade mounted disinfection units may be operated only when the control system detects the presence of occupants in the space. The UV-C lamp units 108a conversely may be operated only when no occupants are detected in the space. This mode of operation applies to all air purification systems and ultraviolet surface sterilization systems disclosed herein.

As noted herein, any of the UVGI disinfection units 100 in any of the embodiments disclosed herein (e.g., ceiling mounted, wall panel mounted, work station partition mounted, etc.) may be used in conjunction with an air filter, and in particular a high-efficiency air filters such as MERV (Minimum Efficiency Reporting Values) filters, electrostatic charged/enhanced particle filters, HEPA (high efficiency particulate air), true HEPA and HEPA-like filters, ULPA (ultra-low particulate air) filters or similar may be used to reduce airborne pathogens. From a practical perspective, MERV 11 through 17 rated filters are preferred in some embodiments since HEPA and ULPA generally get expensive and require a lot of fan energy resulting in increased operating costs. It bears noting that certain embodiments of disinfection units may use high-efficiency filters alone to reduce concentrations of airborne pathogens without UVGI. In certain building facilities or installations, various combinations of the foregoing disinfection units may be used for different purposes and/or at different locations in the facility (e.g., some units with UVGI and high-efficiency air filters, some with UVGI alone, and some with high-efficiency air filters alone) for airborne pathogen control.

While the foregoing description and drawings represent exemplary embodiments of the present disclosure, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made within the scope of the present disclosure. One skilled in the art will further appreciate that the embodiments may be used with many modifications of structure, arrangement, proportions, sizes, materials, and components and otherwise, used in the practice of the disclosure, which are particularly adapted to specific environments and operative requirements without departing from the principles described herein. The presently disclosed embodiments are therefore to be considered in all respects as illustrative and not restrictive. The appended claims should be construed broadly, to include other variants and embodiments of the disclosure, which may be made by those skilled in the art without departing from the scope and range of equivalents.

What is claimed is:

1. A concealed air purification system for an occupiable space of a building, the system comprising:
    a suspended ceiling comprising a support grid hung from a support structure of the building, and a plurality of ceiling panels supported by the support grid;
    a plurality of disinfection units each comprising an ultraviolet light source and at least one fan, the disinfection units mounted above the ceiling panels adjacent to the panels;
    wherein the plurality of disinfection units is configured to draw untreated air from the occupiable space into the disinfection unit from between the panels, disinfect the untreated air, and return treated air to the occupiable space between the panels;
    wherein each disinfection unit is disposed directly adjacent a top surface of a corresponding ceiling panel and supported by the support grid.

2. The system according to claim 1, wherein one of the ceiling panels is interposed between a bottom surface of each disinfection unit and the top surface of the ceiling panel.

3. The system according to claim 1, wherein an air inlet and an air outlet of a housing of each disinfection unit is located directly above correspondingly shaped cutouts at opposing ends of the ceiling panel above which the disinfection unit is mounted.

4. The system according to claim 3, wherein the air inlet and air outlet of each disinfection unit faces downwards towards the occupiable space through the cutouts.

5. The system according to any one of claim 1, further comprising:
    a plurality of linearly elongated narrow utility slots formed by the support grid in the ceiling, the utility slots arranged parallel to each other and disposed between adjoining ceiling panels;
    the disinfection unit having a corresponding narrow width housing having a width about the same as a width of the utility slot;
    wherein the utility slots extend continuously from one wall of the occupiable space to an opposite wall of the space.

6. The system according to claim 5, wherein the housing of each disinfection unit has a length which is greater than four times or more larger than the width of the housing.

7. The system according to claim 5, wherein each disinfection unit comprises an air inlet and an air outlet disposed in the utility slot, each disinfection unit drawing air from and discharging air back to the occupiable space through the utility slot.

8. An air purification system for an occupiable space of a building, the system comprising:
    a suspended ceiling comprising a support grid hung from a support structure of the building;
    a plurality of ceiling panels supported by the support grid; and
    a plurality of disinfection units mounted above the plurality of ceiling panels, each disinfection unit comprising:
        a sterilization source;
        at least one fan;
        an air inlet; and
        an air outlet;
    wherein each air inlet and each air outlet of each disinfection unit is located directly above a correspondingly shaped cutout of a ceiling panel above which the disinfection unit is mounted.

9. The system according to claim 8, wherein the air inlet and the air outlet are located at opposing ends on the disinfection unit.

10. The system according to claim 8, wherein the sterilization source comprises a light source.

11. The system according to claim 10, wherein the light source emits ultraviolet light.

12. The system according to claim 8, further comprising an air filter located of the sterilization source.

13. The system according to claim 8, wherein each disinfection unit is configured to draw untreated air from the occupiable space into the disinfection unit from between the panels, disinfect the untreated air, and return treated air to the occupiable space between the panels.

14. The system according to claim 8, wherein the air inlet and air outlet of each disinfection unit faces downwards towards the occupiable space through the correspondingly shaped cutouts.

15. An air purification system for an occupiable space of a building, the system comprising:
    a support grid hung from a ceiling support structure of the building;
    a plurality of ceiling panels supported by the support grid;
    a plurality of linearly elongated narrow utility slots formed by the support grid in the ceiling, the utility slots arranged parallel to each other and disposed between adjoining ceiling panels; and
    a plurality of disinfection units above the plurality of ceiling panels, each disinfection unit comprising:
        an air inlet;
        an air outlet;
        at least one fan located between the air inlet and the air outlet; and
        a sterilization source in fluid communication with the air inlet and the air outlet.

16. The system according to claim 15, wherein the sterilization source comprises a light source.

17. The system according to claim 16, wherein the light source emits ultraviolet light.

18. The system according to claim 15, wherein the air inlet, air outlet, at least one fan, and sterilization source are concealed within a housing.

19. The system according to claim 15, wherein each disinfection unit comprises a corresponding narrow width housing having a width about the same as a width of the utility slot.

20. The system according to claim 15, wherein each of the utility slots extends continuously from one wall of the occupiable space to an opposite wall of the space.

* * * * *